(12) United States Patent
Watanabe et al.

(10) Patent No.: US 11,302,437 B2
(45) Date of Patent: Apr. 12, 2022

(54) INFORMATION PROCESSING DEVICE, INFORMATION PROCESSING METHOD AND INFORMATION PROCESSING SYSTEM

(71) Applicant: SONY CORPORATION, Tokyo (JP)

(72) Inventors: Shinji Watanabe, Tokyo (JP); Rei Murata, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 170 days.

(21) Appl. No.: 16/462,751

(22) PCT Filed: Nov. 8, 2017

(86) PCT No.: PCT/JP2017/040326
§ 371 (c)(1),
(2) Date: May 21, 2019

(87) PCT Pub. No.: WO2018/105298
PCT Pub. Date: Jun. 14, 2018

(65) Prior Publication Data
US 2020/0066395 A1    Feb. 27, 2020

(30) Foreign Application Priority Data

Dec. 9, 2016  (JP) .............................. JP2016-239254

(51) Int. Cl.
*G16H 30/40* (2018.01)
*G16H 30/20* (2018.01)
(Continued)

(52) U.S. Cl.
CPC ......... *G16H 30/40* (2018.01); *G06K 9/00127* (2013.01); *G06T 7/0012* (2013.01);
(Continued)

(58) Field of Classification Search
CPC .... G16H 30/40; G16H 30/20; G06K 9/00127; G06T 7/0012; G06T 2207/10016;
(Continued)

(56) References Cited

U.S. PATENT DOCUMENTS

2009/0237502 A1    9/2009  Maiya
2010/0251438 A1*   9/2010  Huber ................ G01N 15/1475
                                                    850/1
(Continued)

FOREIGN PATENT DOCUMENTS

CN    101061721 A    10/2007
CN    101548218 A     9/2009
(Continued)

OTHER PUBLICATIONS

International Search Report and Written Opinion of PCT Application No. PCT/JP2017/040326, dated Feb. 13, 2018, 16 pages of ISRWO.

(Continued)

*Primary Examiner* — Marcos L Torres
(74) *Attorney, Agent, or Firm* — Chip Law Group

(57) ABSTRACT

An information processing device according to the present technology includes a determination unit that determines importance related to a cell-specific event of a cell, using image data obtained from a time-series imaging process targeting the cell The information processing device also includes a control unit that controls a process regarding a setting for a target of acquisition of image data in the time-series imaging, on the basis of a determination result of the importance.

19 Claims, 15 Drawing Sheets

(51) Int. Cl.
    *G06K 9/00*         (2022.01)
    *G06T 7/00*         (2017.01)

(52) U.S. Cl.
    CPC ... *G16H 30/20* (2018.01); *G06T 2207/10016* (2013.01); *G06T 2207/10056* (2013.01); *G06T 2207/10148* (2013.01); *G06T 2207/10152* (2013.01); *G06T 2207/30024* (2013.01); *G06T 2207/30044* (2013.01)

(58) Field of Classification Search
    CPC . G06T 2207/10056; G06T 2207/10148; G06T 2207/10152; G06T 2207/30024; G06T 2207/30044; G02B 21/365; G02B 21/36; G01N 33/4833; G01N 21/17; C12M 1/34
    See application file for complete search history.

(56) References Cited

U.S. PATENT DOCUMENTS

| | | |
|---|---|---|
| 2017/0073630 A1 | 3/2017 | Matsubara |
| 2017/0315049 A1 | 11/2017 | Hayashi et al. |
| 2019/0066299 A1 | 2/2019 | Maeda |

FOREIGN PATENT DOCUMENTS

| | | |
|---|---|---|
| CN | 103155549 A | 6/2013 |
| EP | 2085806 A1 | 8/2009 |
| EP | 3150693 A1 | 4/2017 |
| EP | 3460039 A1 | 3/2019 |
| JP | 2006-254270 A | 9/2006 |
| JP | 2008-139488 A | 6/2008 |
| JP | 2008139488 A | 6/2008 |
| JP | 2009-232710 A | 10/2009 |
| JP | 2009232710 A | 10/2009 |
| JP | 2012-095627 A | 5/2012 |
| JP | 201295627 A | 5/2012 |
| JP | 2012095627 A | 5/2012 |
| JP | 2014-042727 A | 3/2014 |
| JP | 2015-223174 A | 12/2015 |
| JP | 2015223174 A | 12/2015 |
| JP | 2017-205053 A | 11/2017 |
| WO | 2016/117638 A1 | 7/2016 |
| WO | 2016117638 A1 | 7/2016 |
| WO | 2016/164857 A1 | 10/2016 |
| WO | 2016164857 A1 | 10/2016 |
| WO | 2016173638 A1 | 11/2016 |
| WO | 2017/199678 A1 | 11/2017 |

OTHER PUBLICATIONS

Extended European Search Report of EP Application No. 17879226.3, dated Nov. 15, 2019, 14 pages.

Office Action for CN Patent Application No. 201780073643.0, dated Jul. 29, 2021, 134 pages of Office Action and 09 pages of English Translation.

* cited by examiner

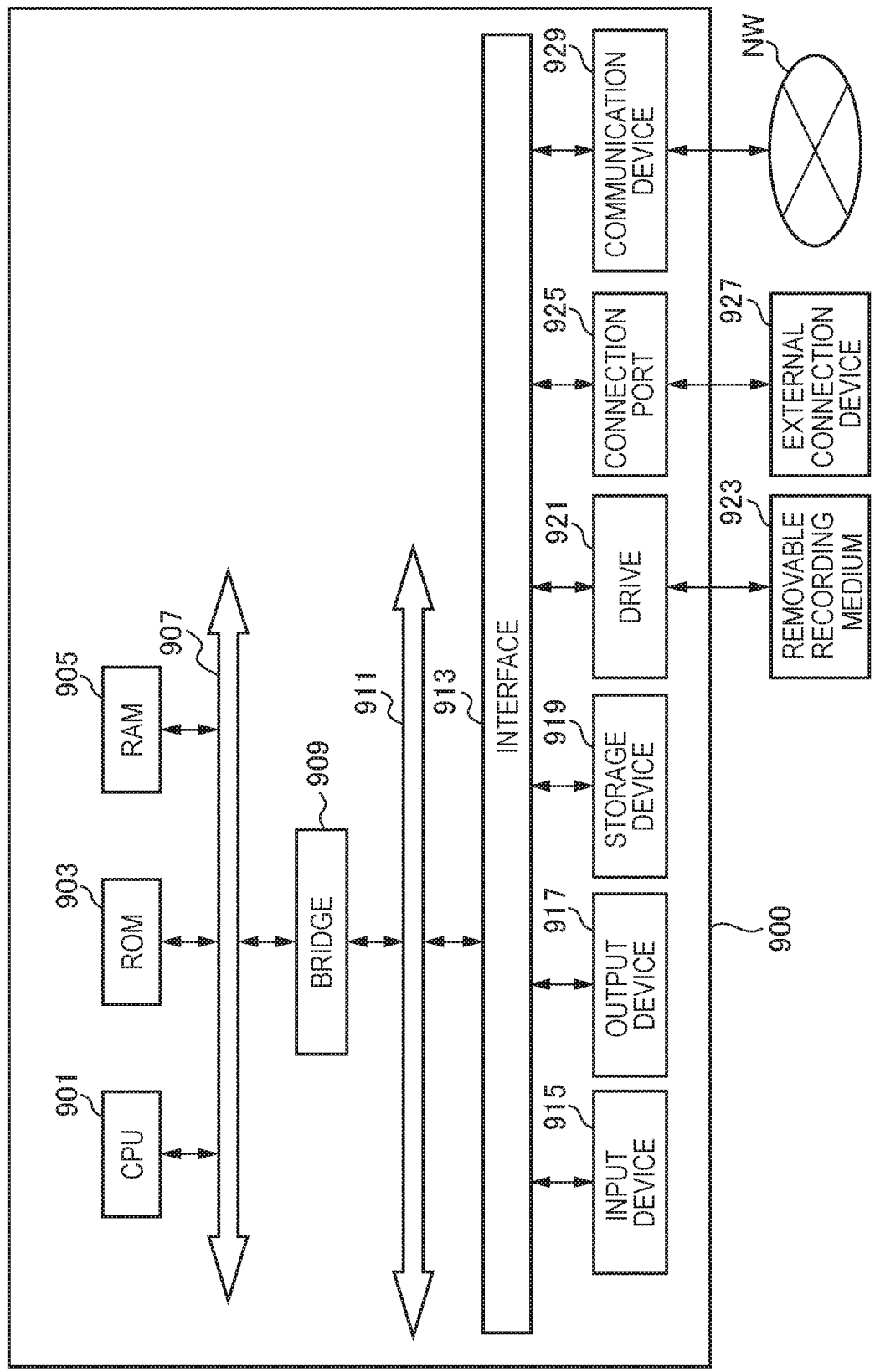

INFORMATION PROCESSING DEVICE, INFORMATION PROCESSING METHOD AND INFORMATION PROCESSING SYSTEM

CROSS REFERENCE TO RELATED APPLICATIONS

This application is a U.S. National Phase of International Patent Application No. PCT/JP2017/040326 filed on Nov. 8, 2017, which claims priority benefit of Japanese Patent Application No. JP 2016-239254 filed in the Japan Patent Office on Dec. 9, 2016. Each of the above-referenced applications is hereby incorporated herein by reference in its entirety.

TECHNICAL FIELD

The present disclosure relates to an information processing device, an information processing method and an information processing system.

BACKGROUND ART

In the fields of medical care and life science, a variety of cells are subjected to image capturing, and motion or change of state of the cells are observed on the basis of the acquired image data. Accumulation of such image data may make it difficult to search image data that represent cell-specific events (for example, cell stage, cleavage occurring at boundaries between cell stages, morphological changes such as cell division, or degeneration) regarding a target cell. In some cases, image data would no more be stored due to strain on the capacity of storage for accumulating image data, possibly missing a chance to acquire image data that represents a valuable event regarding the cell.

Hence, technologies capable of more exactly acquiring image data assumed as a target of acquisition are under development. For example, Patent Literature 1 below discloses a technique by which importance of a medical image is determined under predetermined conditions, in response to an operation signal generated by user's operation, and the medical image is then compressed according to a compressibility of the medical image determined on the basis of such importance. On the other hand, Patent Literature 2 below discloses a technique by which stored video data is erased on the basis of loudness or priority (importance) set by user's operation.

CITATION LIST

Patent Literature

| [Patent Literature 1] | JP 2014-42727A |
| [Patent Literature 2] | JP 2006-254270A |

DISCLOSURE OF INVENTION

Technical Problem

Observation of motion or change of state of the cells, or analysis and evaluation of cell-related events may sometimes take a long period such as several days. This results in production of a huge volume of image data during the observation, overloading the user who manages to determine importance of the image data. It is therefore difficult for the techniques disclosed in aforementioned Patent Literature 1 and Patent Literature 2 to exactly and efficiently store the image data of cells which are acquired by image capturing over a long period.

Hence the present disclosure is to propose a novel and improved information processing device, an information processing method and an information processing system capable of exactly and efficiently store image data of cells, without overloading the user.

Solution to Problem

According to the present disclosure, there is provided an information processing device including: a determination unit that determines importance related to a cell-specific event of a cell, using image data obtained from a time-series imaging process targeting the cell; and a control unit that controls a process regarding setting for a target of acquisition of image data in the time-series imaging process, on the basis of a determination result of the importance.

Moreover, according to the present disclosure, there is provided an information processing method including by a processor: determining importance related to a cell-specific event of a cell, using image data obtained from a time-series imaging process targeting the cell; and controlling a process regarding setting for a target of acquisition of image data in the time-series imaging process, on the basis of a determination result of the importance.

Moreover, according to the present disclosure, there is provided an information processing system including: an imaging device that includes an imaging unit that produces an image by image capturing; and an information processing device that includes a determination unit that determines importance related to a cell-specific event of a cell, using image data obtained from a time-series imaging process targeting the cell by the imaging unit; and a control unit that controls a process regarding setting for a target of acquisition of image data in the time-series imaging process, on the basis of a determination result of the importance.

Advantageous Effects of Invention

As explained above, the present disclosure makes it possible to store image data of cells in a certain and efficient manner, without overloading the user.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 15 is a block diagram illustrating an exemplary hardware configuration of an information processing device according to an embodiment of the present disclosure.

MODE (S) FOR CARRYING OUT THE INVENTION

Figure 1:
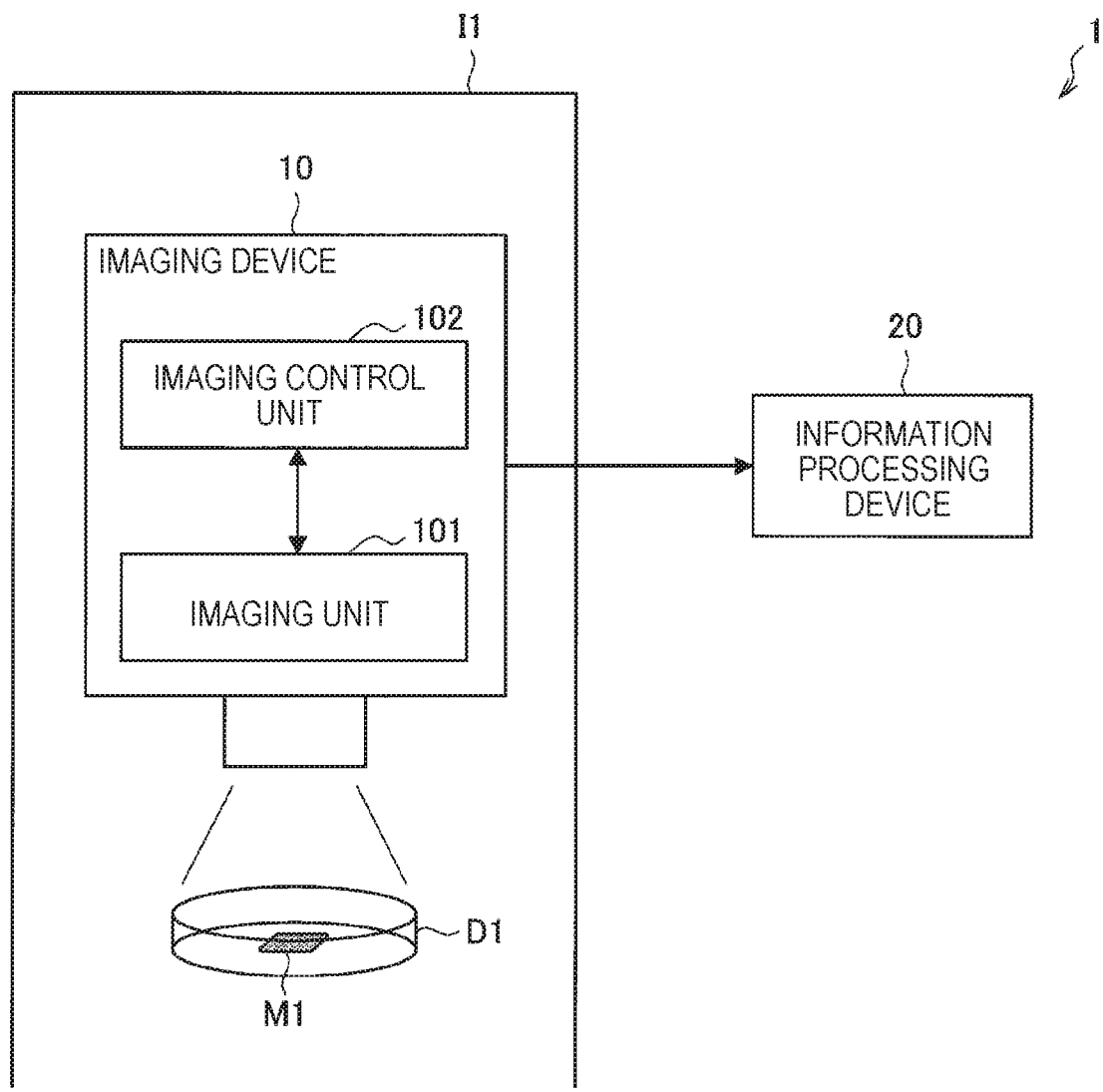
FIG. 1 is a diagram illustrating an overview of a configuration of an information processing system according to an embodiment of the present disclosure.

Hereinafter, (a) preferred embodiment (s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Now, the description will be made following the order below.
1. Overview of Information Processing System
2. First Embodiment
  2.1. Exemplary Configuration
  2.2. Exemplary Processing
3. Second Embodiment
  3.1. Exemplary Configuration
  3.2. Exemplary Processing
4. Exemplary Hardware Configuration
5. Conclusion FIG. 1 is a diagram illustrating an overview of a configuration of an information processing system 1 according to an embodiment of the present disclosure. As illustrated in FIG. 1, the information processing system 1 has an imaging device 10, and an information processing device 20. The imaging device 10 and the information processing device 20 are connected through a variety of wired or wireless networks.

(Imaging Device)

The imaging device 10 is a device that produces images (for example, still images or video) by image capturing. The imaging device 10 according to the embodiment is typically embodied by a digital camera. The imaging device 10 may alternatively be embodied by any of devices with imaging function, such as smartphone, tablet, game machine or wearable device.

The imaging device 10 according to the embodiment is provided, as illustrated in FIG. 1, inside a culture incubator I1, above a dish D1 that contains a medium M1 in which cell to be observed is cultured. The imaging device 10 captures images of the cell cultured in the medium M1 at a predetermined frame rate, to thereby produce image data. Now, in a case where a plurality of cells is present in the dish D1, the cells may be captured so as to be contained one by one in imaging frames, or may be captured so that a plurality of cells is contained in a single imaging frame. On the other hand, in a case where a plurality of cells is individually cultured in a plurality of dishes, it is also possible to capture images of each cell, while suitably moving the imaging device 10 or the dishes using a freely selectable driving unit provided to the incubator I1.

Now, the imaging device 10 may be provided inside the incubator I1, or outside the incubator I1. Alternatively, the imaging device 10 is applicable to image capturing of cells which are not housed in the incubator I1. Still alternatively, the imaging device 10 may be provided integrally with the incubator I1.

In addition, the incubator I1 is not specifically limited in terms of specification or size, thus allowing use of any incubator which is capable of providing an environment suitable for culturing cell. Also regarding the dish D1 and the medium M1, those publicly-known to be suitable for culturing cell are employable.

In more details, the imaging device 10 according to the embodiment has an imaging unit 101 and an imaging control unit 102, as illustrated in FIG. 1.

The imaging unit 101 has various components including an image sensor such as CCD (Charge Coupled Device) or CMOS (Complementary Metal Oxide Semiconductor), a lens that controls focusing of an object image on the image sensor, and a light source that illuminates an object, and captures images of real space using these components.

In order to correctly specify motion inside the cell to be observed, the imaging unit 101 according to the embodiment captures images of a predetermined imaging region that contains cell (s) cultured on the medium M1. The imaging unit 101 may capture images of cell directly (without being interposed by other component, such as lens), or may capture images of cell while being interposed by other component such as a microscope with an objective lens. In this design, the objective lens preferably has a magnification of 40× to 60× or around, for the purpose of capturing motion of cell in sub-micron order. While the frame rate is not specifically limited, it is preferably set depending on the extent of changes of a target to be observed. More specifically, the frame rate is preferably set to a value so that motion of cell in sub-second order may be captured.

The imaging unit 101 may be provided with a plurality of imaging modules. More specifically, the imaging device 10 may be provided with an imaging module for time-lapse capturing and an imaging module for video shooting described later. With such design, it now becomes possible to produce image data that satisfy performances, including picture quality, individually required for the time-lapse images and video.

A signal generated as a result of imaging process by the imaging unit 101 is output to the imaging control unit 102.

The imaging control unit 102 has a processing circuit built up with a CPU (Central Processing Unit), ROM (Read Only Memory), a RAM (Random Access Memory) and so forth; and a communication device, and controls entire operations of the imaging unit 101. The imaging control unit 102 typically controls capturing by the imaging unit 101, and generates image data on the basis of a signal obtained from the capturing process.

For example, the imaging control unit 102 can control the timing the imaging unit 101 carries out the imaging process. More specifically, the imaging control unit 102 can control the imaging unit 101 to carry out the imaging process intermittently at predetermined intervals (so-called, time-lapse imaging). The imaging control unit 102 can also control the imaging unit 101 to carry out imaging process continuously over a predetermined period so as to produce video data. Alternatively, the imaging control unit 102 may change, add, or delete the timing according to which the imaging unit 101 carries out image capturing of cells, in response to a command output from the information processing device 20, which will be detailed later.

Meanwhile, in a case where a plurality of cells is captured, the imaging control unit 102 may directly or indirectly control the incubator I1 so as to move the imaging device 10 or the dish according to the capture timing of the cells to be captured. Note that an exemplary control of the timing of capturing process according to one embodiment of the present disclosure will be described later.

Alternatively, the imaging control unit 102 may control the wavelength, illumination intensity or illumination time of the light source provided to the imaging unit 101. For example, the imaging control unit 102 may control the light source of the imaging unit 101, so as to illuminate cell with light of appropriate wavelength at minimum illumination intensity, only within a period the imaging unit 101 is capturing images. This can minimize phototoxicity on cell.

Still alternatively, the imaging control unit 102 may allow the imaging unit 101 to carry out the imaging process, while controlling the distance between the dish D1 and the imaging device 10, typically with the aid of a stage provided to the incubator I1. In this way, slice images (so-called, Z-stack image) or confocal image assumed as the target to be observed may be produced. This enables three dimensional structural analysis of the target to be observed.

Now as will be detailed later, the imaging control unit 102 may preliminarily set a region of interest (ROI) on images. The region of interest in this context means a region subjected to the later-described image analysis carried out by the image analysis unit 202. The region of interest in this embodiment is a region corresponded, for example, to intracellular tissues (cytoplasm, nucleus, etc.) or peripheral tissues (cell membrane). More specifically, if the target to be observed is an embryo, the region of interest is preferably an internal region of the embryo, and particularly a region corresponded to cytoplasm of the embryo. How to set the region of interest and so forth will be described later.

The imaging control unit 102 outputs the produced image data and so forth to the information processing device 20. Note such image data may be recorded in an unillustrated storage owned by the imaging device 10, or may be recorded in an external server, cloud or storage different from the information processing device 20.

(Information Processing Device)

The information processing device 20 is a device having an image analyzing function. The information processing device 20 may be embodied by various devices having image analyzing function, including PC (Personal Computer), tablet and smartphone. The information processing device 20 contains a processing circuit such as CPU (Central Processing Unit), and a communication device which includes hardware allowed for wireless or wired communication. For example, in the information processing device 20 according to this embodiment, the communication device acquires, from the imaging device 10, image data targeted at a cell obtained in the time-series imaging process. The processing circuit then determines, on the basis of the acquired image data, importance related to a cell-specific event regarding the cell. The processing circuit then controls, on the basis of the determination result of importance, a process regarding setting for a target of acquisition of image data in the time-series imaging process. Result of such process is output typically to the imaging device 10, or to the internal or external storage device of the information processing device 20. Note that the information processing device 20 may be embodied by one or a plurality of information processing devices on a network. A functional configuration for realizing the respective functions of the information processing device 20 will be described below.

Note that, although the information processing system 1 in the embodiment includes the imaging device 10 and the information processing device 20, the present technology is not limited to this design. For example, the imaging device 10 may take part in processing regarding the information processing device 20 (for example, determination process, setting process, or the like). In this design, the information processing system 1 is embodies by an imaging device having, for example, a determination function.

Now the cell, which is an exemplary cell to be applied by the information processing system 1 according to the embodiment, will be explained. For example, a normal human fertilized egg shows a pronucleus that appears immediately after fertilization, and then starts cell division. Note that, although the fertilized egg is not an embryo but pronuclear-stage embryo in the strict sense, the present specification will also deal the fertilized egg as one form of embryo.

In cleavage, a normal fertilized egg (embryo) initially in the 1-cell stage cleaves to produce a 2-cell stage embryo, then repeats cleavage to produce a 4-cell embryo, 8-cell embryo, morula, to reach blastocyst finally over several days. In the normal course, the blastocyst adheres to a uterus, the pellucida that surrounds the embryo breaks, and the embryo thus hatches. That is, the timing of cleavage can be deemed to be one checkpoint of embryogenetic stage. The cleavage and the events demonstrated in embryo development stages are examples of the cell-specific event. As is clear from above, the cell-specific event means any events that are demonstrated by cells on the basis of physiological function intrinsically or genetically owned by the cells. The cell-specific event may include events demonstrated in response to physical, chemical or electromagnetic stimulation. For example, also an event demonstrated as a result of medicinal effect of a drug administered to the cell may be included in the cell-specific event.

As a technique for evaluating growth of embryo, having been developed is, for example, a technique of observing or analyzing image data obtained by successively capturing images of embryo. Evaluation of growth of embryo, however, takes at least several days, during which a huge volume of image data generated in the imaging process will be accumulated in the storage or the like. This makes it difficult to search among the huge volume of image data to find out image data that represents a target event regarding the embryo. Moreover, strain on the capacity of storage or the like may possibly inhibit storage of image data. In particular in observation of cells such as embryo, overwriting of past image data is not desirable, from the viewpoint of supporting accuracy of the evaluation.

As a countermeasure for the aforementioned problem, for example, JP 2014-42727A and JP 2006-254270A disclose techniques of compressing or deleting image data, on the basis of importance (priority) preset by user's operation or the like. Culture duration of cells such as embryo, however, ranges at least over several days as described above. Image data produced in the duration will be huge, and will overload the user with a task to determine which image data need be compressed or deleted (that is, how to preset importance).

Now, the information processing system 1 according to this embodiment determines importance related to a cell-specific event regarding a cell, using image data generated in the time-series imaging process targeting the cell, and controls a process regarding the setting for a target of acquisition of image data in the time-series imaging process, on the basis of the determination result of importance. As will be explained in the embodiments below, the process regarding the setting for a target of acquisition of image data includes a process of presetting time point of generation of image data (that is, preset of timing of image capturing of cells in a real-time processing), and determination of a target of storage of the produced image data (that is, determination of image data to be stored or deleted in post-processing). In this way, the importance may be determined on the basis of the event regarding cell contained in the image data, making it possible to efficiently and exactly store image data regarding event specially desired to be observed by the user. Hence, it now becomes possible to evaluate motion or change of state of cells even after the imaging process ranged over a long period, without overloading the user.

The overview of the information processing system 1 according to one embodiment of the present disclosure has been described above. Now the individual embodiments below will explain exemplary applications of the present technology, focusing embryo as one example of the cell. The present technology is, however, not limited to these examples. For example, the information processing system 1 according to the embodiment is also applicable to cell, biotissue and so forth capable of demonstrating morphological changes specific to living bodies, such as those causing cell division, or such as those incorporating other cell or the like. In addition, besides embryonic cleavage, the events regarding cells to which the present technique is applied can include proliferation or division of cancer cell, nerve cell, ES cell, iPS cell and other cells; differentiation of stem cell; and morphological changes of immune cell and other cells. In addition, the target to which the information processing system 1 according to this embodiment is applied may be not only cells, but may also be biological samples such as biological tissues. Alternatively, the target to which the information processing system 1 according to this embodiment is applied may be animal, plant or inanimate structures. For example, any structural or morphological changes that will occur over several hours or several days on the basis of events specific to the target to be observed, including proliferation or metamorphosis of living body, or growth of thin film or nano-cluster crystal, are possible targets of application of the information processing system 1 according to this embodiment.

The information processing device 20 contained in the information processing system 1 according to one embodiment of the present disclosure is embodied in the embodiment below. Specific examples of configuration and processing of the information processing device 20 will be explained below.

2. FIRST EMBODIMENT

The first embodiment of the present disclosure will be explained referring to FIG. 2 to FIG. 12. In the information processing system 1 according to this embodiment, there are a determination process of importance using the image data obtained from the imaging process, and a process regarding the setting for a target of acquisition of image data in the imaging process on the basis of importance, which are carried out concurrently with the imaging process in the imaging device 10. In this way, it now becomes possible to selectively produce image data considered to be important in the aforementioned imaging process. The image data may therefore be stored efficiently and more exactly, without overloading the user.

<2.1. Exemplary Configuration>

Figure 2:
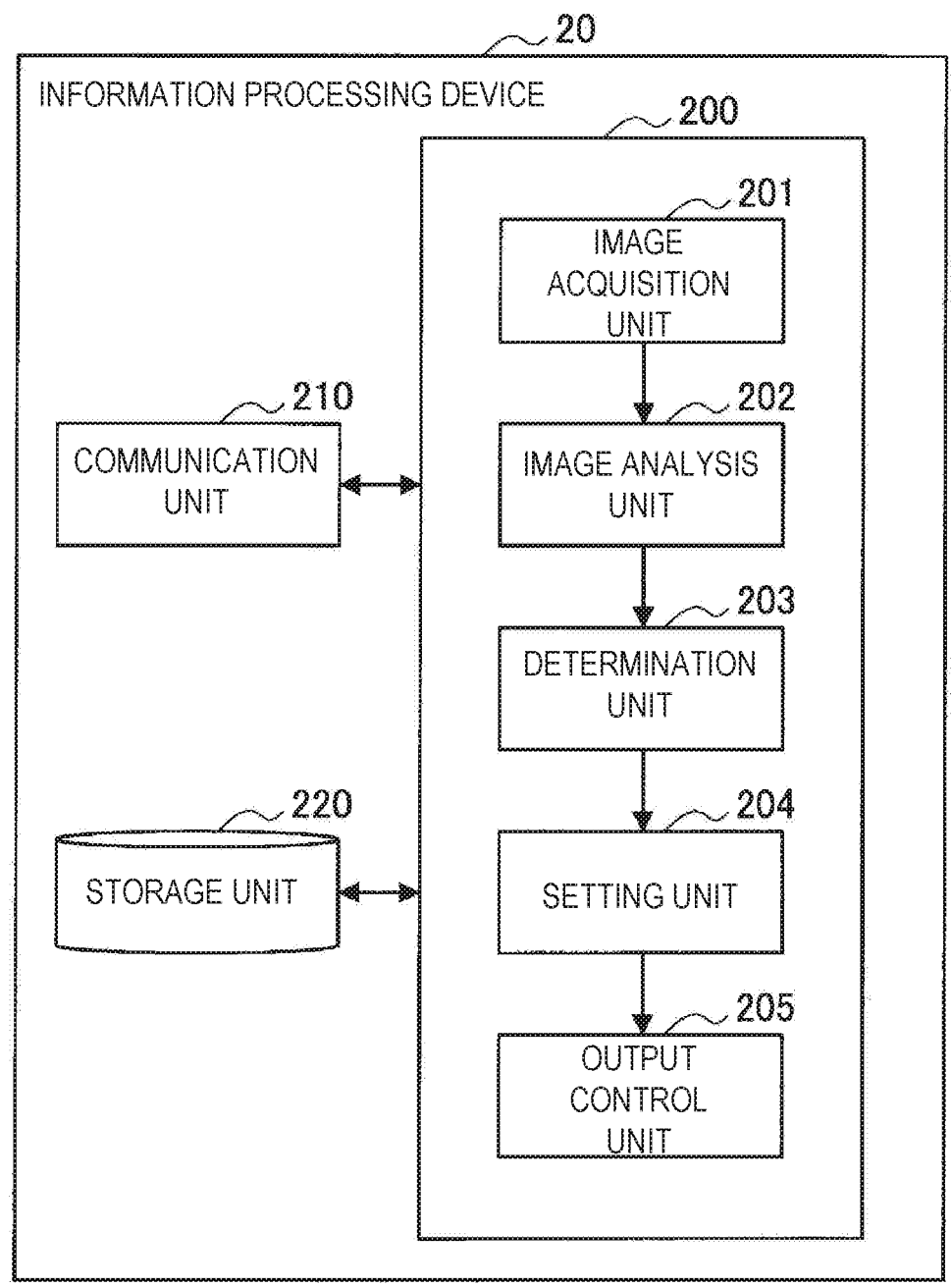
FIG. 2 is a functional block diagram illustrating an exemplary functional configuration of an information processing device according to a first embodiment of the present disclosure.

FIG. 2 is a functional block diagram illustrating an exemplary functional configuration of the information processing device 20 according to the first embodiment of the present disclosure. As illustrated in FIG. 2, the information processing device 20 according to the embodiment has a control unit 200, a communication unit 210 and a storage unit 220. The individual function units will be explained below.

(Control Unit)

The control unit 200 controls entire operations of the information processing device 20. Further, as illustrated in FIG. 2, the control unit 200 has the individual functions of an image acquisition unit 201, an image analysis unit 202, a determination unit 203, a setting unit 204, and an output control unit 205, and controls operations of the information processing device 20 according to the embodiment in a leading manner. The functions of the individual functional units contained in the control unit 200 will be described later. The control unit 200 is typically embodied by a processing circuit such as CPU.

(Communication Unit)

The communication unit 210 is a communication means possessed by the information processing device 20, and takes part in various types of communications in a wired or wireless manner, through a network (or directly), with an external device. For example, the communication unit 210 communicates with the imaging device 10. More specifically, the communication unit 210 acquires image data produced by the imaging device 10. Alternatively, the communication unit 210 may communicate with a device other than the imaging device 10. For example, the communication unit 210 may send images acquired by the image acquisition unit 201, information regarding proposal controlled by the output control unit 205, and so forth to an external display device or the like. The communication unit 210 is typically embodied by a communication device such as communication antenna combined with RF (Radio Frequency) circuit (wireless communication), an IEEE 802.15.1 port combined with a transceiver circuit (wireless communication), an IEEE 802.11b port combined with a transceiver circuit (wireless communication), or a LAN (Local Area Network) terminal combined with a transceiver circuit (wired communication).

(Storage Unit)

The storage unit 220 is a storage device installed in the information processing device 20 and stores information acquired by the communication unit 210, information obtained by the respective function units of the control unit 200, and the like. For example, the storage unit 220 can store the image data acquired from the imaging device 10 through the communication unit 210. Further, the storage unit 220 appropriately outputs the stored information in response to a request from each function unit of the control unit 200 or from the communication unit 210. In addition, the storage unit 220 carries out a process regarding image data stored in the storage unit 220 (for example, output of image data to the control unit 200, acquisition of image data from the control unit 200, and deletion of image data), in response to a command issued from the control unit 200. The storage unit 220 is typically embodied by a magnetic recording medium such as hard disk, or a nonvolatile memory such as flash memory. Alternatively, the storage unit 220 may be embodied for example by an external cloud server or storage. In this design, the information processing device 20 is not necessarily provided with the storage unit 220.

Next, the functions of the respective function units installed in the control unit 200 will be described.
(Image Acquisition Unit)

The image acquisition unit 201 has a function that acts to acquire, from the imaging device 10, image data produced in the time-series imaging process targeting the cell. The image data is acquired through the communication unit 210.

The image data produced in the time-series imaging process in this context means, for example, image data of time-lapse image. The time-lapse image is a series of still images obtained from the imaging process carried out intermittently at predetermined intervals.

Examples of preset conditions for the imaging process for the time-lapse image are listed in Table 1. In blastocyst analysis of embryo (analysis of embryonic growth) assumed as a target to be observed according to this embodiment, the time-lapse image is obtained by repetitively capturing image of embryo at 15 minute intervals. The imaging process can be continued, for example, over 5 days. Conditions for such imaging process of time-lapse image can suitably be preset depending on details of analysis of the target to be observed as listed in Table 1. For example, in the imaging process for analyzing migration ability of cancer cell, the imaging intervals can be one hour, and the process period can be one week. Meanwhile, in the imaging process for analyzing cocultivation with iPS cell, the imaging intervals can be 10 minutes, and the process period can be one month.

TABLE 1

| Analysis of target to be observed | Analysis of blastocyst | Analysis of migration ability of cancer cell | Analysis of cocultivation with iPS cell |
|---|---|---|---|
| Imaging intervals | 15 Minutes | 1 Hour | 10 Minutes |
| Process period of imaging process | 5 Days | 1 Week | 1 Month |
| Continuous imaging time (of video) | 10 Seconds | 10 Seconds | 10 Seconds |

On the basis of such conditions for the imaging process, a timeline regarding the imaging process of time-lapse image is set. The timeline according to this embodiment means time-series information that determines a target of generation of image data (target of acquisition) in the time-series imaging process, which is preset from the viewpoint of data size. The timeline can contain timing of imaging in the imaging process, number of shooting (Z-stack image) per a single timing of imaging, or information regarding resolution or compressibility of the image data that is expected to be produced.

For example, the timeline regarding analysis of embryo development stages listed in Table 1 is a timeline that represents image capturing repeated at 15 minute intervals over a process period of imaging process of 5 days. Such timeline may suitably be modified by the setting unit 204 described later.

Note that the aforementioned image data is not limited to the time-lapse image, but may be image data of video. The video contains images in a plurality of successive frames obtained by continuous image shooting over a predetermined period. Such video may be a video obtained by seamless image shooting that takes place from the start through the end of shooting, but may preferably be a video obtained by continuous image shooting that takes place only for a predetermined period, and at predetermined intervals, taking phototoxicity and image processing load into consideration. In this embodiment, the plurality of images that composes the video can be those produced by continuous image shooting that takes place over several seconds to several tens of seconds, at a frame rate of several to several tens of frames per second.

For example, as listed in Table 1, in the analysis of embryo development stages assumed as the target to be observed according to this embodiment, video is obtained by 10-second-long continuous shooting of embryo, repeated at 15 minute intervals. In this case, the aforementioned time-lapse image may be an image of one frame extracted from a plurality of imaging frames that compose the video. The thus extracted image of one frame may be, for example, an image in the first frame, among from a plurality of imaging frames that composes the video.

Note that the image data may be image data regarding one or a plurality of embryos. The image data regarding the plurality of embryos mean image data that contain the plurality of embryos one by one in imaging frames, or image data that contains the plurality of embryos in a single imaging frame.

The image acquisition unit 201 according to this embodiment acquires, for example, image data that contains an embryo captured by the imaging unit 101 of the imaging device 10. More specifically, the image acquisition unit 201 according to this embodiment can acquire, through the communication unit 210, an image that contains an embryo captured at a predetermined timing of imaging in a real-time manner by the imaging unit 101 of the imaging device 10, according to a preset timeline. In this case, the determination process for determining importance, and the setting process for setting the target of generation of image data in the individual functional units in the succeeding stage may be carried out in a real-time manner.

Note that although the timeline according to this embodiment will be explained assuming that it will be used for controlling the timing of imaging in the imaging process carried out by the imaging control unit 102 of the imaging device 10, the present technology is not limited to this example. That is, the timeline may alternatively be used for determining image data to be acquired from the imaging device 10 of the image acquisition unit 201. Note, however, that for the case of setting the timeline for increasing the timing of imaging as described later, the preset timeline can be used to control the timing of imaging in the imaging process carried out by the imaging control unit 102.

Note that, for the purpose improving accuracy of the determination process, the image acquisition unit 201 may properly carry out calculation typically for interpolation, noise removal, and correction such as rotation, of the acquired image.

The image acquisition unit 201 outputs the acquired image data to the image analysis unit 202.

(Image Analysis Unit)

The image analysis unit 202 has a function of analyzing the image data. For example, the image analysis unit 202 can set a region of interest (ROI) on an image of embryo contained in the image data, can carry out image analysis in the region of interest, and can calculate feature of the region of interest.

Figure 3:
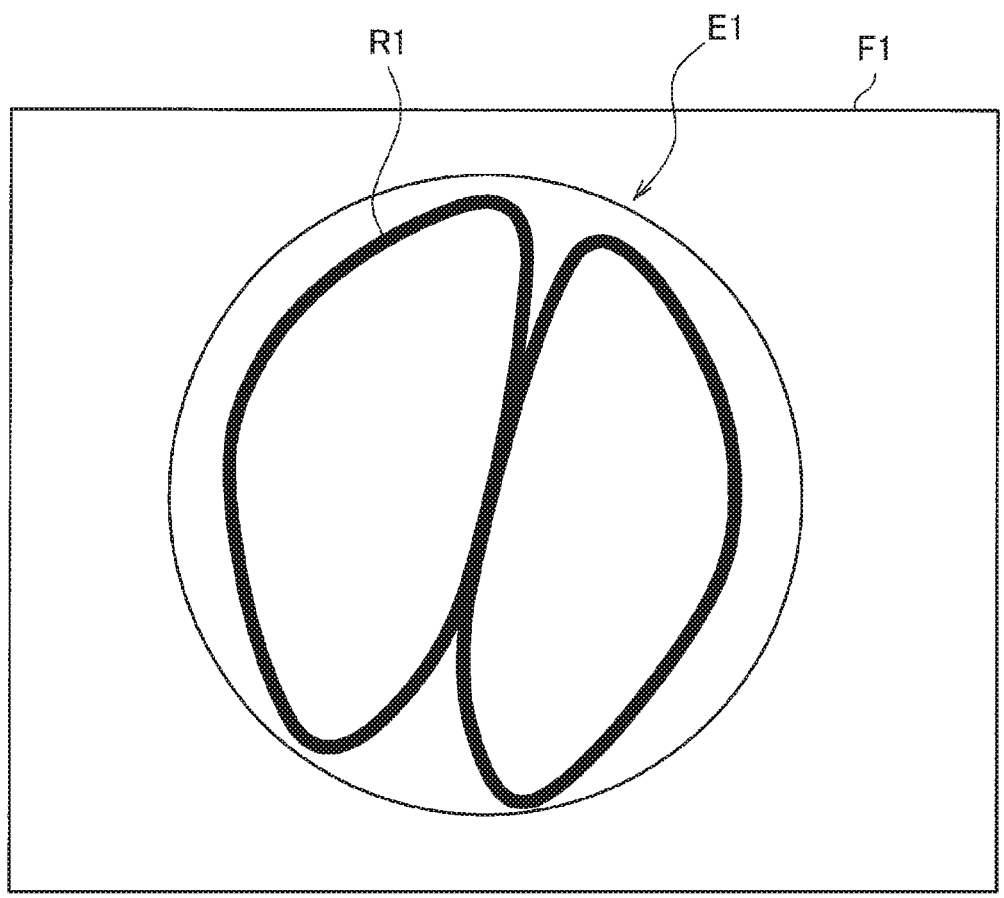
FIG. 3 is a drawing explaining an exemplary setting of a region of interest in an image analysis unit according to this embodiment.

The region of interest means a region to be analyzed in the succeeding process, in an occupied area of the image. FIG. 3 is a drawing for explaining an exemplary setting of a region of interest in the image analysis unit 202 according to this embodiment. As illustrated in FIG. 3, the region of interest R1 according to this embodiment is a region that corresponds to the inside of embryo E1 contained in the image F1. The inside of embryo E1 may specifically mean the cytoplasm contained in a central part of embryo E1. With such design, it now becomes possible to specify motion of the embryonic cytoplasm by an analytical process or the like in the succeeding stage. Note that, for an exemplary case where also geometrical changes in embryo need be analyzed, the region of interest may be defined not only by cytoplasm, but also by pellucida (a part assumed as an interface to the outside field).

The image analysis unit 202 may preset the region of interest, typically according to operation by the user made on an unillustrated input device (for example, known input devices such as mouse, touch pen and touch panel). Alternatively, the image analysis unit 202 may preset the region of interest, by using freely selectable image analysis technologies typically based on known algorithms including image thresholding, Hough transformation and machine learning. Still alternatively, the image analysis unit 202 may preset the region of interest for a plurality of images, by estimating how the region of interest preset to a single image can move over the plurality of images, using an algorithm such as optical flow. With such design, it now becomes possible to automatically preset the region of interest for the plurality of images in which the motion inside the embryo will be analyzed.

Alternatively, processes for presetting the region of interest for video may, for example, be performed preliminarily by other device having information processing function, such as the imaging device 10. In this case, the function of the image analysis unit 202, regarding presetting of the region of interest, may be left unused.

The image analysis unit 202 can carry out image analysis in the preset region of interest regarding embryo, and can calculate feature of the region of interest. The feature includes, for example, feature based on morphology of the region of interest, feature based on motion (kinetics) of the region of interest, and feature based on pixel information of image. The morphology of the region of interest means morphology of embryo that corresponds to the region of interest, or mode of the inside of embryo (cytoplasm), and the feature based on the morphology of the region of interest is a feature obtained from one still image. On the other hand, the motion of the region of interest includes motion resulted from morphological change of embryo that corresponds to the region of interest, and from modal change inside embryo that corresponds to the region of interest, and the feature is obtained from a plurality of images.

The feature based on morphology of the region of interest is exemplified by area, circumferential length, circularity, long axial length or short axial length of the region of interest; or, changes in average, dynamic range, variance or standard deviation of luminance. Meanwhile, the feature based on motion of the region of interest is exemplified by feature that represents morphological change of embryo that corresponds to the region of interest, and feature that represents modal change inside embryo. More specifically, the feature that represents morphological change of embryo that corresponds to the region of interest is exemplified by area, circumferential length, circularity, long axial length or short axial length of the region of interest; or, changes in average, dynamic range, variance or standard deviation of luminance. Meanwhile, the feature that represents modal change inside embryo that corresponds to the region of interest is exemplified by average, acceleration, standard deviation, travel range, maximum value, minimum value or median of motion within the region of interest. Furthermore, the feature based on pixel information of image is exemplified by luminance histogram or frequency spectrum.

In this embodiment, a plurality of features may be calculated by image analysis. For example, the image analysis unit 202 may calculate the feature based on morphology of the region of interest (for example, variance of image), feature that represents modal change inside embryo that corresponds to the region of interest (for example, average of motion), and feature that represents morphological change of embryo that corresponds to the region of interest (for example, change in the circumferential length of the region of interest). Acquisition of a plurality of features will improve accuracy of determination in the determination unit 203 in the succeeding stage.

Such image analysis can be performed using any of known techniques. For example, motion vector may be analyzed in order to calculate the motion size within the region of interest. The motion vector can be acquired using any of known algorithms such as block matching method or gradient method. Alternatively, morphology and so forth in the region of interest may be analyzed by any of known techniques, on the basis of pixel information of the image.

The image analysis unit 202 outputs the featured obtained by the image analysis to the determination unit 203.

(Determination Unit)

The determination unit 203 has a function of determining importance related to the cell-specific event regarding cell, using the image data.

The determination unit 203 according to this embodiment can discriminate the embryo-specific event regarding embryo, on the basis of the feature calculated by the image analysis unit 202. Then the determination unit 203 according to this embodiment can determine importance on the basis of such determination result.

Figure 4:
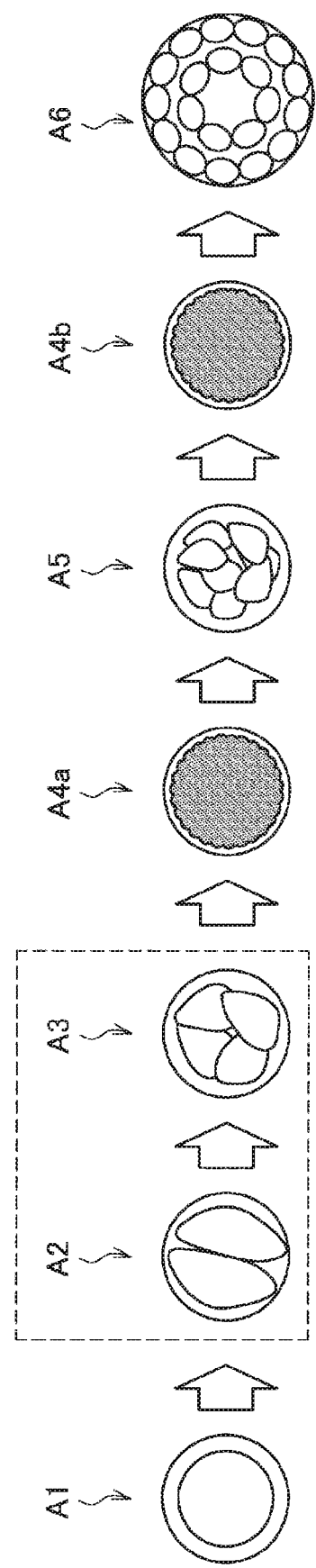
FIG. 4 is a schematic drawing illustrating an exemplary flow of embryo development stages.

Now the embryo-specific event regarding embryo and the importance will be explained. The embryo-specific event regarding embryo according to this embodiment means embryo development stages. FIG. 4 is a schematic drawing illustrating an exemplary flow of embryo development stages. In FIG. 4, states A1 to A6 respectively represent embryo development stages listed in Table 2 below. Note that there may be a stage of morula between states A5, A4*b* and A6. Also note that in a case where states immediately before and immediately after cleavage are discriminable even within the same cell stage, the embryo development stage can be classified, for example, into early period or late period of the cell stage. Such ranks of stages can appropriately be preset depending on the cell-specific event.

TABLE 2

| State | Embryo development stages |
|---|---|
| A1 | 1-Cell stage |
| A2 | 2-Cell stage |
| A3 | 4-Cell stage |
| A4a | Cleavage in process |
| A5 | 8-Cell stage |
| A4b | Cleavage in process |
| A6 | Blastocyst |

The importance determined in this embodiment means importance related to the embryo development stages determined from image data. An assumable case is that the 2-cell stage (state A2) and the 4-cell stage (state A3), enclosed by a broken line in FIG. 4, are desired to be observed in greater detail. In this case, if an image of embryo contained in image data is determined to be in state A2 or state A3, the determination unit 203 assigns high importance to the image data. Note that the number of ranks or weight that represents the degree of importance may appropriately be set. This embodiment will be explained referring to cases where the importance is ranked on a three-point scale of "high", "medium" and "low", or on a two-point scale of "high" and "low". The rank of importance is, however, not limited to this example.

Figure 5:
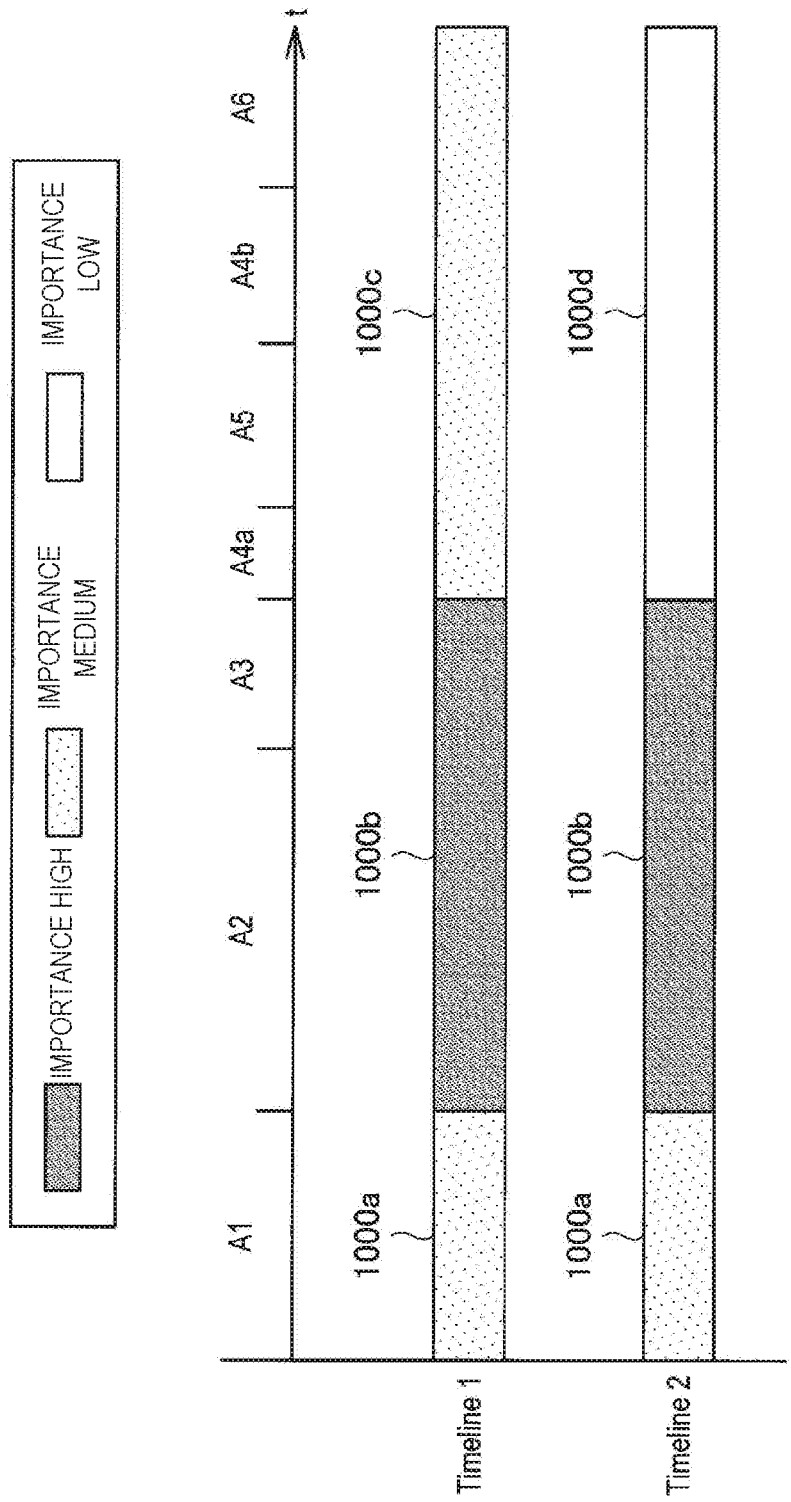
FIG. 5 is a graph illustrating an exemplary relation between embryo development stages and importance in a timeline of imaging process.

FIG. 5 is a graph illustrating an exemplary relation between the embryo development stages and the importance in the timeline of the imaging process. Notations of A1 to A6 in FIG. 5 correspond to the states that represent the embryo development stages shown in FIG. 4 and Table 2. For example, as shown in Timeline 1, a possible way is that high importance is assigned to time zone 1000b that represents the embryo development stages given by state A2 and state A3, and (relatively) low importance is assigned to the residual time zones 1000a and 1000c. In this way, the setting unit 204 and the output control unit 205 in the succeeding stage are now enabled to preferentially produce image data and so forth in the time zone assigned with high importance.

Alternatively, for the case as illustrated in Timeline 2 where the image data regarding the embryo development stages in state A4a and thereafter are not necessary, a possible way is that much lower importance is assigned to state A4a and thereafter. In this way, the frequency of image capturing in, for example, time zone 1000d may further be lowered, or the imaging process per se may be stopped.

In order to embody the timeline as illustrated in FIG. 5 in a real-time process, the key is to determine the importance corresponding to the successive embryo development stages. The determination unit 203 according to this embodiment determines the importance of the embryo development stages contained in image data, using analytical result (feature) obtained from the image analysis unit 202. In this way, even in a long timeline that ranges over several days, an appropriate timeline for imaging process may be set without overloading the user. Note that the preset of the timeline may be given by a function of the setting unit 204 in the succeeding stage.

A method of determining the importance by the determination unit 203 according to this embodiment will be explained. For example, the determination unit 203 determines the importance on the basis of at least one feature acquired from the image analysis unit 202. More specifically, the determination unit 203 may discriminate the embryo development stages by applying the feature acquired from the image analysis unit 202, to a learned model that has learned a relation between the embryo development stages and the individual features. The learned model is a model constructed typically by using the embryo development stages as a response variable, and using the individual features as an explanatory variable. Technique regarding such learning may be any of known techniques, such as a neural network based on deep learning or the like.

Alternatively, even in a case where the aforementioned model is not used, the determination unit 203 may determine the importance by using the size of the thus acquired feature as an index, and by comparing the index with a predetermined threshold value. The predetermined threshold value may appropriately be preset so as to be corresponded to the aforementioned embryo development stages. In this way, Otherwise, the determination unit 203 can be embodied by any of known technologies of image analysis, so long as the importance related to embryo development stages can be determined from image data.

Note that the determination unit 203 may carry out the determination process by using not only a single image data, but also image data in the frames preceding and succeeding that image data. In this way, the embryo development stages will be determined more exactly, and the accuracy of determination of importance will be improved.

The determination unit 203 outputs information regarding the thus determined importance to the setting unit 204.

(Setting Unit)

The setting unit 204 has a function of providing settings regarding a target of acquisition of image data in the time-series imaging process, on the basis of the determination result of importance. The settings regarding a target of acquisition of image data, carried out by the setting unit 204 according to this embodiment mean two processes, namely (1) setting for target temporal unit, and (2) setting for target of generation (target of acquisition).

(1) Setting for Target Temporal Unit

The setting unit 204 according to this embodiment sets a target temporal unit regarding the target of generation of image data, on the basis of a process period for imaging process by the imaging device 10. The setting for target temporal unit in this context means setting for target temporal unit by ranking the timeline illustrated in FIG. 5 by the importance, that is, updating the timeline for imaging process depending on the importance. The setting unit 204 according to this embodiment can update the timeline, corresponding to the thus determined importance.

Figure 6:
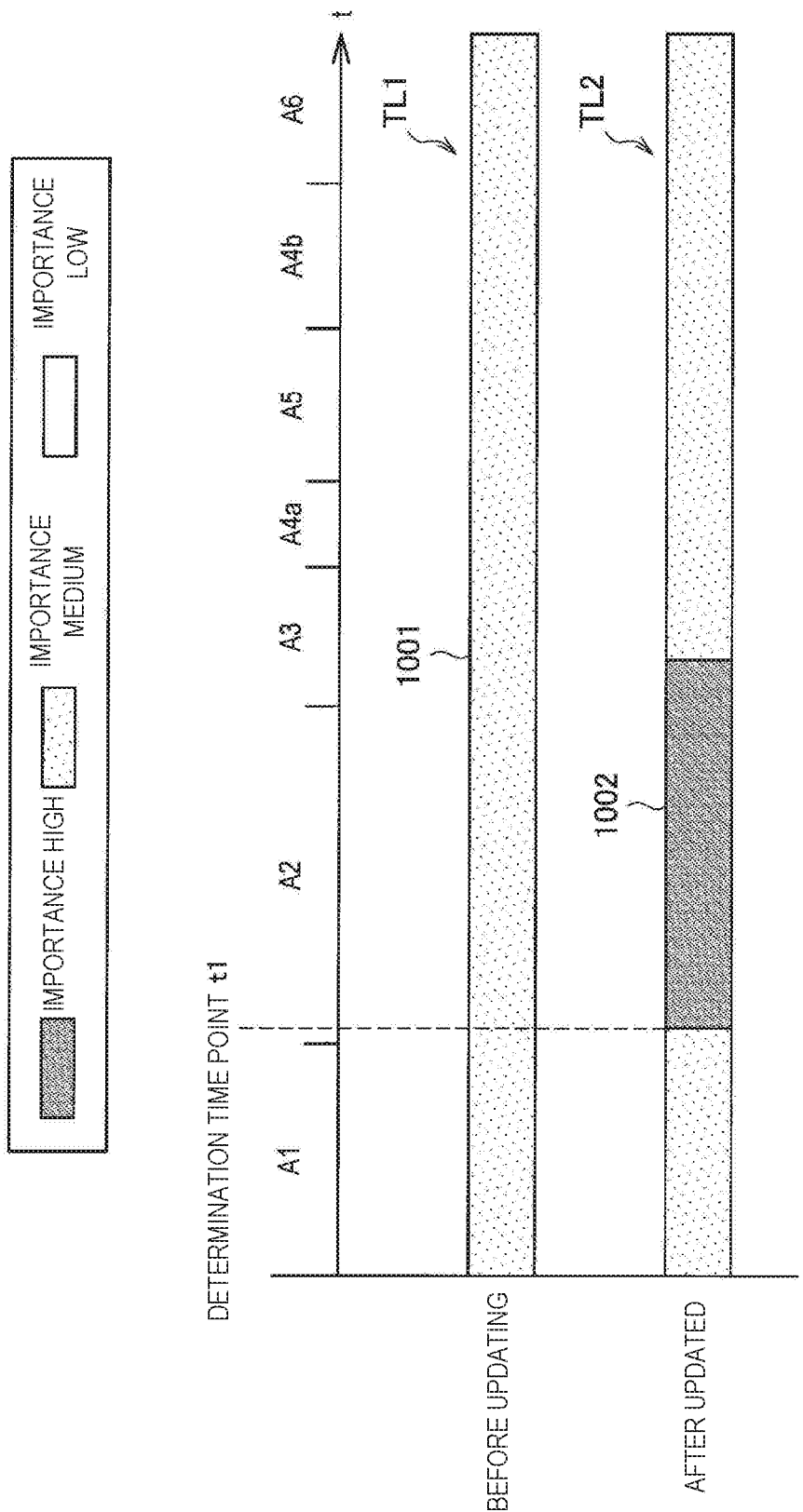
FIG. 6 is a graph illustrating an exemplary updating process for the timeline at determination time point $t_1$ carried out by the setting unit according to this embodiment.
Figure 7:
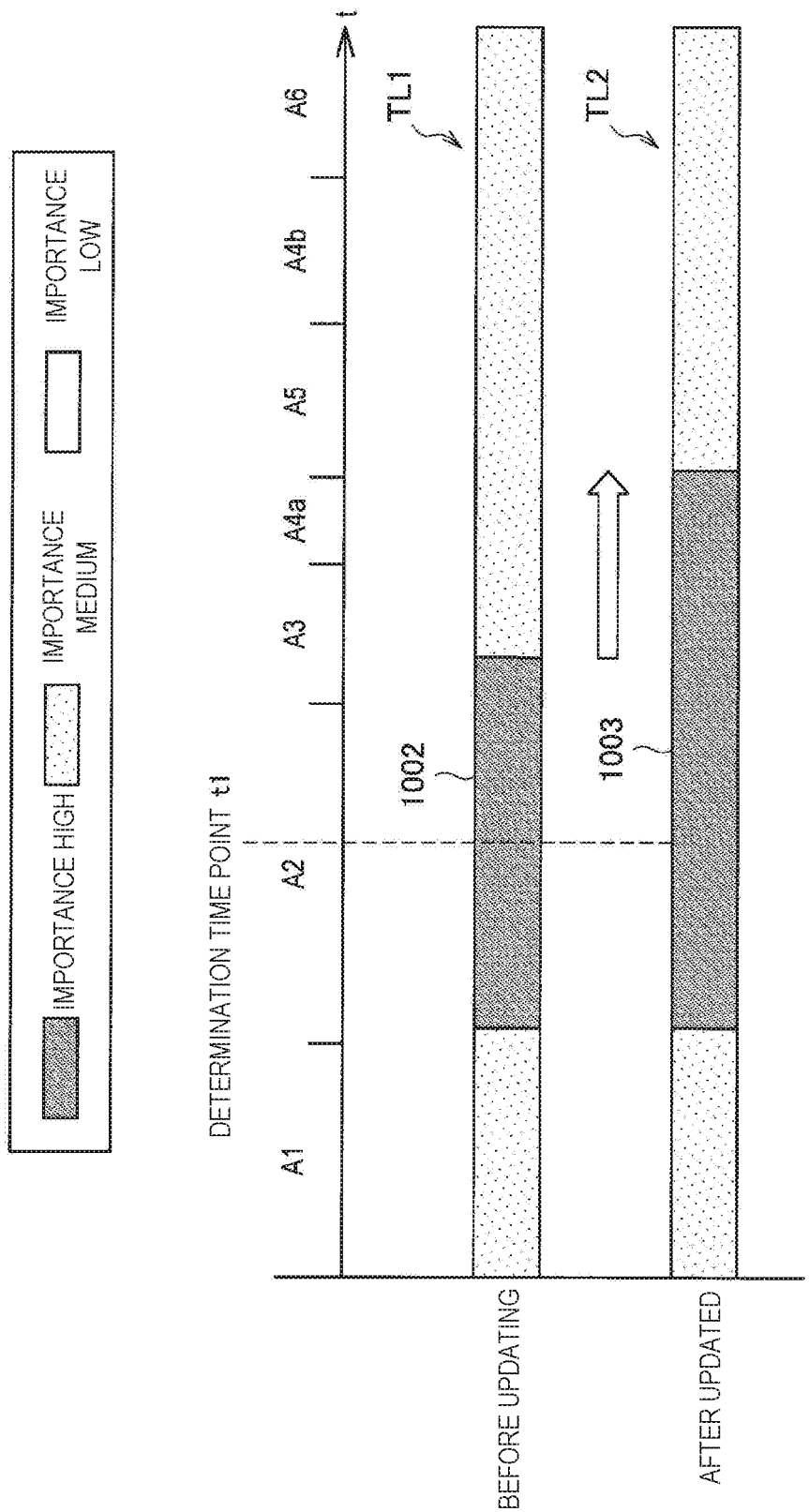
FIG. 7 is a graph illustrating an exemplary updating process for the timeline at determination time point $t_2$ carried out by the setting unit according to this embodiment.
Figure 8:
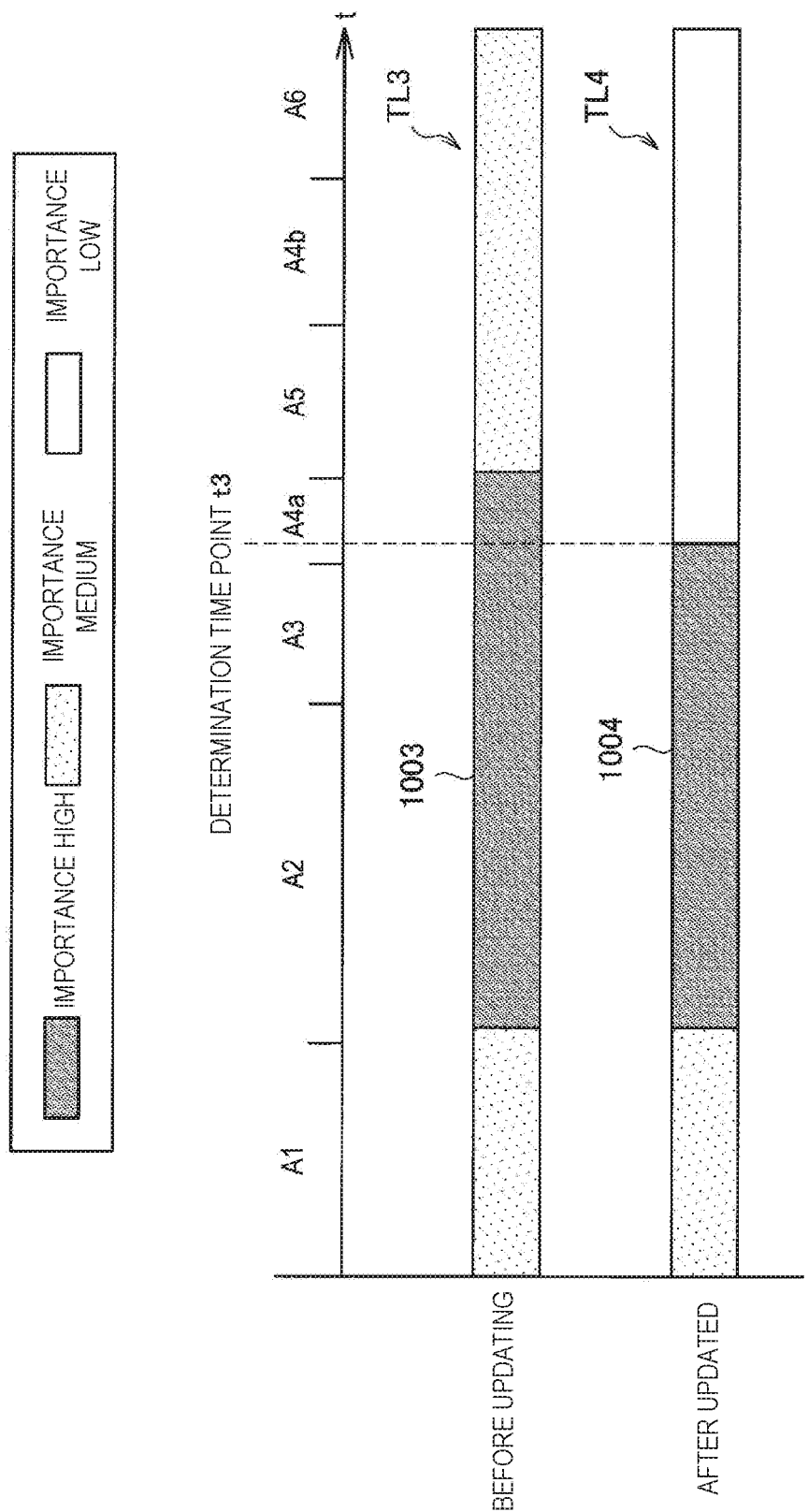
FIG. 8 is a graph illustrating an exemplary updating process for the timeline at determination time point $t_3$ carried out by the setting unit according to this embodiment.

Now, the setting process of the target temporal unit carried out by the setting unit 204 will be explained referring to FIG. 6 to FIG. 8. FIG. 6 to FIG. 8 are graphs illustrating exemplary updating processes at time points of judgment $t_1$, $t_2$ and $t_3$, carried out by the setting unit 204 according to this embodiment. Note that in this updating process, the importance will be explained as being ranked on a three-point scale of "high", "medium" and "low". Meanwhile, the determination time point means time point of imaging regarding target image data to be analyzed by the image analysis unit 202. In this example, judgment of state A2 and state A3 will be assigned with "high" importance, judgment of state A will be assigned with "medium" importance, and judgment of state D1 and thereafter will be assigned with "low" importance.

First, in timeline TL1 before updating illustrated in FIG. 6, the importance is uniformly set to "medium" throughout the process period of imaging process (bar 1001). Now assume that, at determination time point $t_1$, the embryo development stage contained in the image data is determined to have state A2 (2-cell stage) by the determination unit 203, with the importance of "high". The setting unit 204 then sets a target temporal unit with the importance of "high", at the determination time point $t_1$ and thereafter (bar 1002). The setting unit 204 thus yields updated timeline TL2.

Alternatively, the setting unit 204 may further update the timeline having been updated once. Assuming that, during the imaging process sustained according to timeline TL2 as illustrated in FIG. 7, the embryo development stage contained in the image data is determined again to have state A2a at determination time point $t_2$ by the determination unit 203, with the importance of "high". Then the setting unit 204 may further extend the target temporal unit with the importance of "high" (bar 1003). In the thus updated timeline TL3, the end point of the target temporal unit can further be put off.

Alternatively, assuming that, during the imaging process sustained according to timeline TL3 as illustrated in FIG. 8, the embryo development stage contained in the image data is determined to have state D1 at determination time point $t_3$ by the determination unit 203, with the importance of "low". The setting unit 204 then sets a target temporal unit with the importance of "low", at the determination time point $t_3$ and thereafter (bar 1004). In this way, the frequency of image capturing and so forth may be reduced or the imaging process per se may be stopped at determination time point $t_3$ and thereafter, and the temporal unit that falls on the time point and thereafter can be excluded from the target of acquisition of image data.

As described above, by appropriately updating the target temporal unit using the importance determined by the determination unit 203, enabled is real-time setting for the target of generation in the later-described image capturing.

Note that the length of target temporal unit may, for example, be a predetermined length (more specifically, length corresponded to intervals of the time-lapse imaging, for example). Alternatively, the length of the target temporal unit may appropriately be controlled corresponding to the embryo development stages (that is, the cell-specific event) determined by the determination unit 203. Still alternatively, the length of target temporal unit may be controlled on the basis of the feature calculated in image analysis carried out by the image analysis unit 202. For an exemplary case where cells after administered with a drug need be observed regarding an event such as medical efficacy, the timing at which the changes will appear over a long period of imaging process may vary depending on types of drug. Hence by setting the target temporal unit on the basis of the determined embryo development stages or calculated feature, the temporal unit with high importance (or low importance) may be determined in a more appropriate manner. Similarly, the length of extended unit may be a predetermined length like the aforementioned length of target temporal unit, or may be set corresponding to the embryo development stages determined by the determination unit 203.

Note that the time points of judgment illustrated in FIG. 6 to FIG. 8 are merely for exemplary purposes. For example, the determination unit 203 may carry out the determination process assuming all time points of imaging set on the timeline as the determination time point, or assuming at least one time point selected from a plurality of time points of imaging as the determination time point. The setting unit 204 can appropriately set the target temporal unit, using the importance obtained as a result of the determination process carried out by the determination unit 203. Also note that, although the target temporal unit corresponded to the importance is not set in timeline TL1 before updating in FIG. 6, the target temporal unit may be set preliminarily depending on the importance, even for the timeline before being subjected to the setting process carried out by the setting unit 204.

(2) Setting for Target of Generation

The setting unit 204 according to this embodiment also sets the target of generation of image data (target of acquisition) in the time-series imaging process. Now the setting for the target of generation of image data means setting for the target of generation of image data in the time-series imaging process, or setting of increase or decrease of data size of producible image data.

Figure 9:
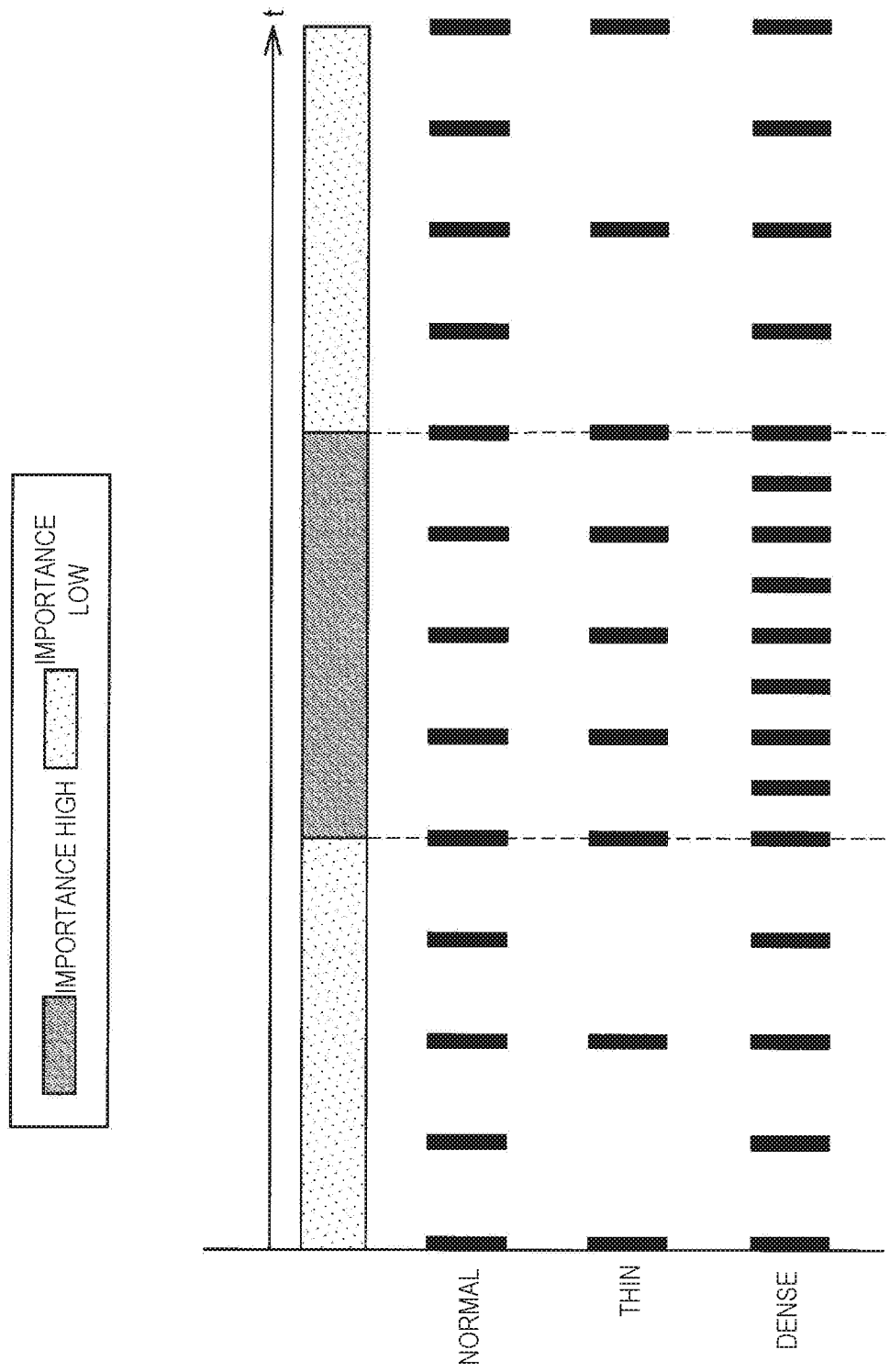
FIG. 9 is a graph illustrating a first example of the setting for a target of generation, carried out by the setting unit according to this embodiment.

In this embodiment, the setting for target of generation means, for example, deletion or addition of the timing of imaging in the time-series imaging process. FIG. 9 is a graph illustrating a first example of the setting for the target of generation carried out by the setting unit 204 according to this embodiment. Referring to FIG. 9, the timeline regarding the time-series imaging process initially has, as seen in "normal", the timing of imaging which is set at regular intervals. After the importance is determined by the determination unit 203, and the target temporal unit is set according to the importance by the setting unit 204, the setting unit 204 can update the timing of imaging depending on the importance.

For example in a timeline named "thin", the setting unit 204 can make the setting so as to delete the timing of imaging in the temporal unit of "low" importance. In this way, the image data regarding the cell-specific events which are not important in observation of cells, may be suppressed from being accumulated. In addition, upon switching of the temporal unit of "low" importance into the temporal unit of "medium" importance, the setting unit 204 may return the timing of imaging back to the intervals in the initial timeline. This helps to maintain quality of the acquired image data.

On the other hand in a timeline named "dense", the setting unit 204 can make the setting so as to add the timing of imaging in the temporal unit of "high" importance. In this way, the image data regarding events, which are important in observation of cells, may be accumulated intensively. Alternatively, the setting unit 204 may reduce the timing of imaging from the original plan in the temporal unit of "low" importance, and may increase the timing of imaging from the original plan in the temporal unit of "high" importance.

Alternatively as explained above, the setting unit 204 may delete the timing of imaging at a predetermined time point and thereafter, on the basis of the importance. That is, the setting unit 204 may make setting so as to stop the imaging process at a predetermined time point and thereafter. This helps to suppress unnecessary image data regarding the cell-specific events which need not be observed, from being accumulated.

Figure 10:
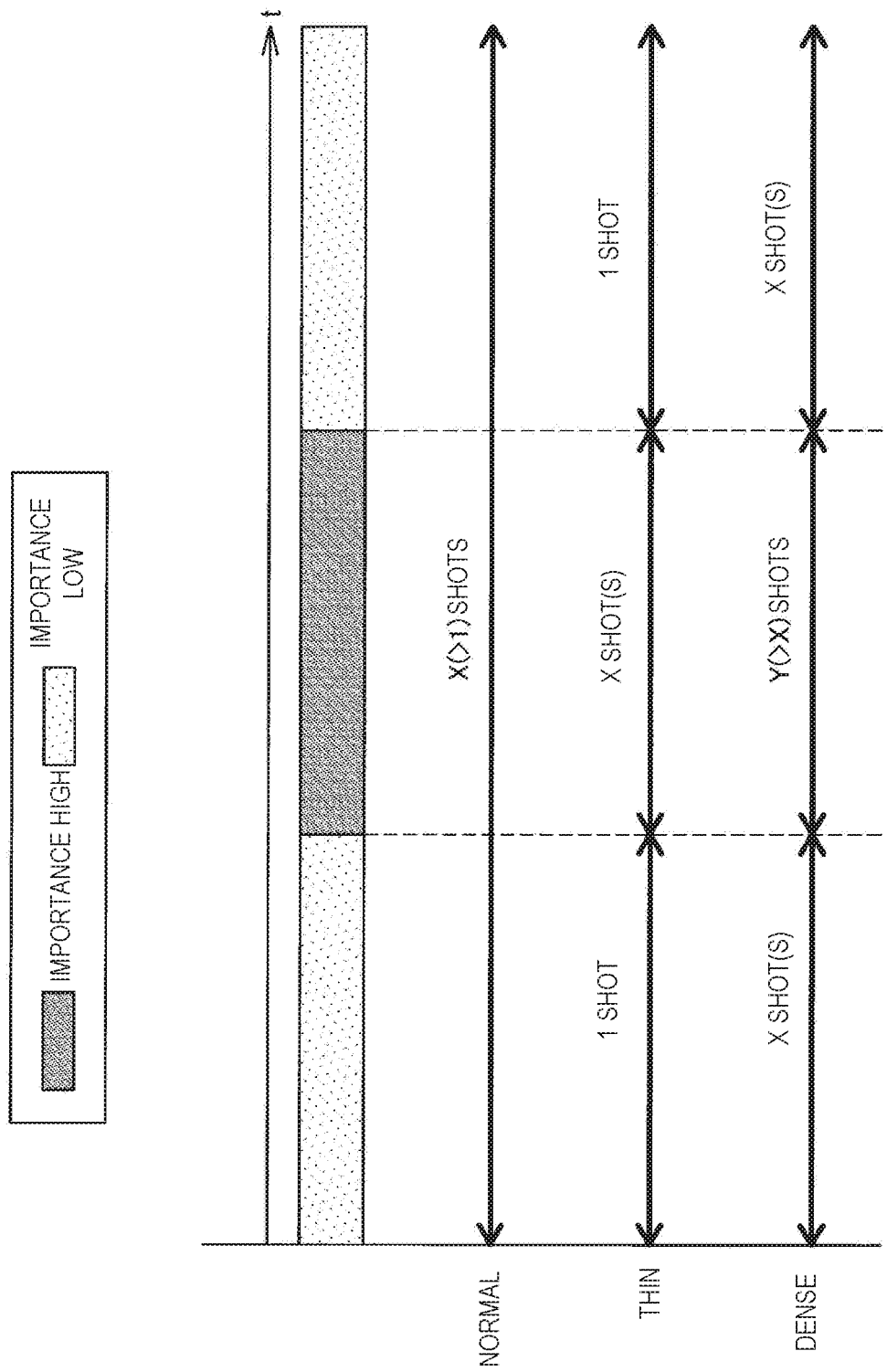
FIG. 10 is a graph illustrating a second example of the setting for a target of generation, carried out by the setting unit according to this embodiment.

In addition, in a case where image data of Z-stack image (a plurality of images obtainable at one time point by multiple imaging at different focal positions) is generable in the time-series imaging process, the setting for the target of generation may include setting of the number of shots (number of acquisition) and focal position of the Z-stack image. FIG. 10 is a graph illustrating a second example of the setting for the target of generation, carried out by the setting unit 204 according to this embodiment. Referring to FIG. 10, the timeline regarding the time-series imaging process initially has, as seen in "normal", the number of shots of Z-stack image which is set to X (>1) shots. After the importance is determined by the determination unit 203, and the target temporal unit is set according to the importance by the setting unit 204, the setting unit 204 can update the number of shots of Z-stack image depending on the importance.

For example, in the "thin" timeline, the setting unit 204 can make the setting so as to decrease the number of shots of Z-stack image in the temporal unit of "low" importance (for example, 1 shot). At the same time, also the focal position of producible Z-stack image can be set depending on the preset number of shots. Specific setting of focal position can be made depending on types of cell assumed as the target to be observed, cell-specific event and so forth. In this way, the image data regarding cell-specific events which are not important in observation of cells, may be suppressed from being accumulated.

Meanwhile, in the "dense" timeline, the setting unit 204 can make the setting so as to increase the number of shots of Z-stack image in the temporal unit of "high" importance. At the same time, also the focal position of producible Z-stack image can be set depending on the preset number of shots. In this way, the image data regarding events, which are important in observation of cells, may be accumulated intensively. Alternatively, the setting unit 204 may reduce the number of shots from the original plan in the temporal unit of "low" importance, and may increase the number of shots from the original plan in the temporal unit of "high" importance.

In addition in this embodiment, also a process regarding increase or decrease of data size of the image data to be produced can take place. Such increase or decrease of data size of image data to be produced means increase or decrease of resolution or compressibility of the generable image data. More specifically, the setting unit 204 may set high resolution or low compressibility for image data generable in the temporal unit with high importance. Meanwhile, the setting unit 204 may set low resolution and high compressibility for image data generable in the temporal unit with low importance.

Figure 11:
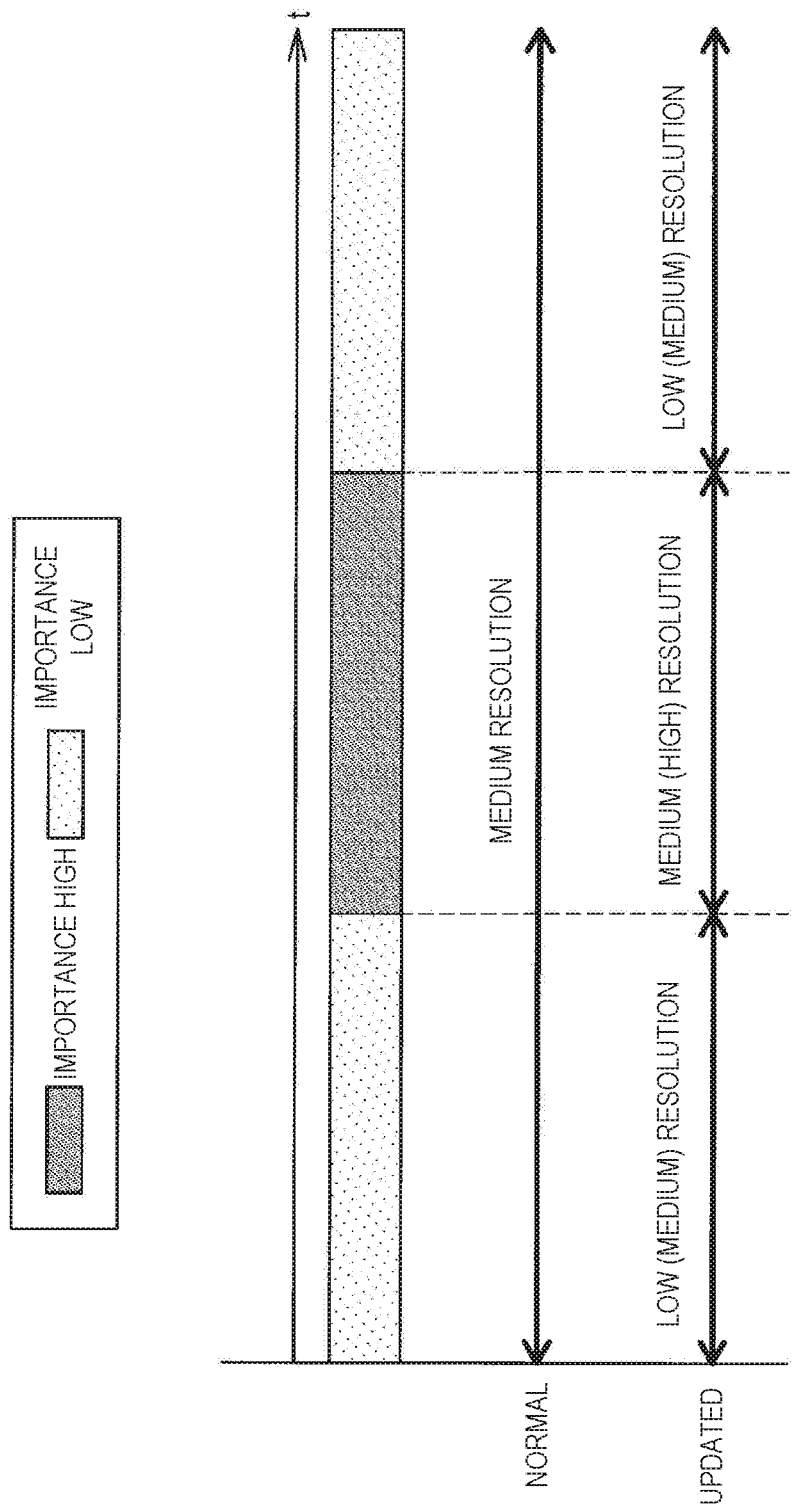
FIG. 11 is a graph illustrating a third example of the setting for a target of generation, carried out by the setting unit according to this embodiment.

FIG. 11 is a graph illustrating a third example of the setting for the target of generation carried out by the setting unit 204 according to this embodiment. Referring to FIG. 11, the timeline regarding the time-series imaging process initially has, as seen in "normal", the resolution of the generable image data which is set to medium resolution.

Then after the importance is determined by the determination unit 203, and the target temporal unit is set according to the importance by the setting unit 204, the setting unit 204 can update the resolution of the generable image data depending on the importance. More specifically, as seen in an "updated" timeline illustrated in FIG. 11, the setting unit 204 can set the resolution to low resolution (or medium resolution) in the temporal unit with "low" importance. Meanwhile, the setting unit 204 can set the resolution to medium resolution (or high resolution) in the temporal unit with "high" importance. In this way, the data size of the image data regarding the cell-specific events, which are not important in observation of cells, may be reduced, and the quality of image data regarding events, which are important in observation of cells, may be enhanced preferentially.

As described above, as a result of the (updating) setting of the timeline corresponded to the importance carried out by the setting unit 204, the image data primarily containing the time-lapse image that represents a target cell-specific event to be observed may be acquired in an exact and efficient manner.

Note that, there may be a case where the setting process of timeline by the setting unit 204 will not be carried out, depending on the determination result given by the determination unit 203. For example, in a case where the determination result on the importance given by the determination unit 203 is identical to the immediately previous determination result, and the target temporal unit and so forth need not be updated, the setting process of timeline by the setting unit 204 may be omissible.

The setting unit 204 outputs information that is based on the setting thus acquired in the setting process, to the output control unit 205.

(Output Control Unit)

The output control unit 205 has a function of controlling an output as a result of processes in the control unit 200. For example, the output control unit 205 according to this embodiment controls to output information that is based on the setting acquired from the setting unit 204. More specifically, the output control unit 205 outputs the information based on the aforementioned setting to the imaging control unit 102 of the imaging device 10, through the communication unit 210. Such information based on the setting include information regarding the timeline of the time-series imaging process updated by the setting unit 204. Upon acquisition of the information, the imaging control unit 102 carries out the imaging process according to the updated timeline. That is, the imaging control unit 102 can carry out the imaging process, according to the timing of imaging, the number of shots of Z-stack image, or image quality (increase or decrease of data size) which are specified by the timeline.

Alternatively, the output control unit 205 may output the information based on the setting to the image acquisition unit 201. In this case, the image acquisition unit 201 will acquire, from the imaging device 10, only the image data preset as a target of acquisition, according to the updated timeline. This consequently makes it possible to reduce the target image data assumed as a target of generation, or to reduce the data size of the produced image data, although the imaging process per se is not controlled.

The construction of the control unit 200 according to this embodiment has been explained. As the individual functional units equipped to such control unit 200 repetitively carry out the determination process for importance using image data, and the setting process for target of generation, concurrently with the imaging process carried out by the imaging device 10, the timeline corresponded to the importance is sequentially updated to control the imaging process. This consequently makes it possible to store the image data that represents a cell-specific event which is desired to be observed, in an efficient and exact manner, without overloading the user even in prolonged observation. In addition, the target of generation of image data may optionally be decreased or increased, making it possible to suppress phototoxicity possibly exerted on the cell during image capturing of the cell.

<2.2. Exemplary Process>

The configuration and the functions of the information processing device 20 according to the embodiment have been described above. Next, an exemplary process performed by the information processing device 20 according to the embodiment will be described referring to FIG. 12.

Figure 12:
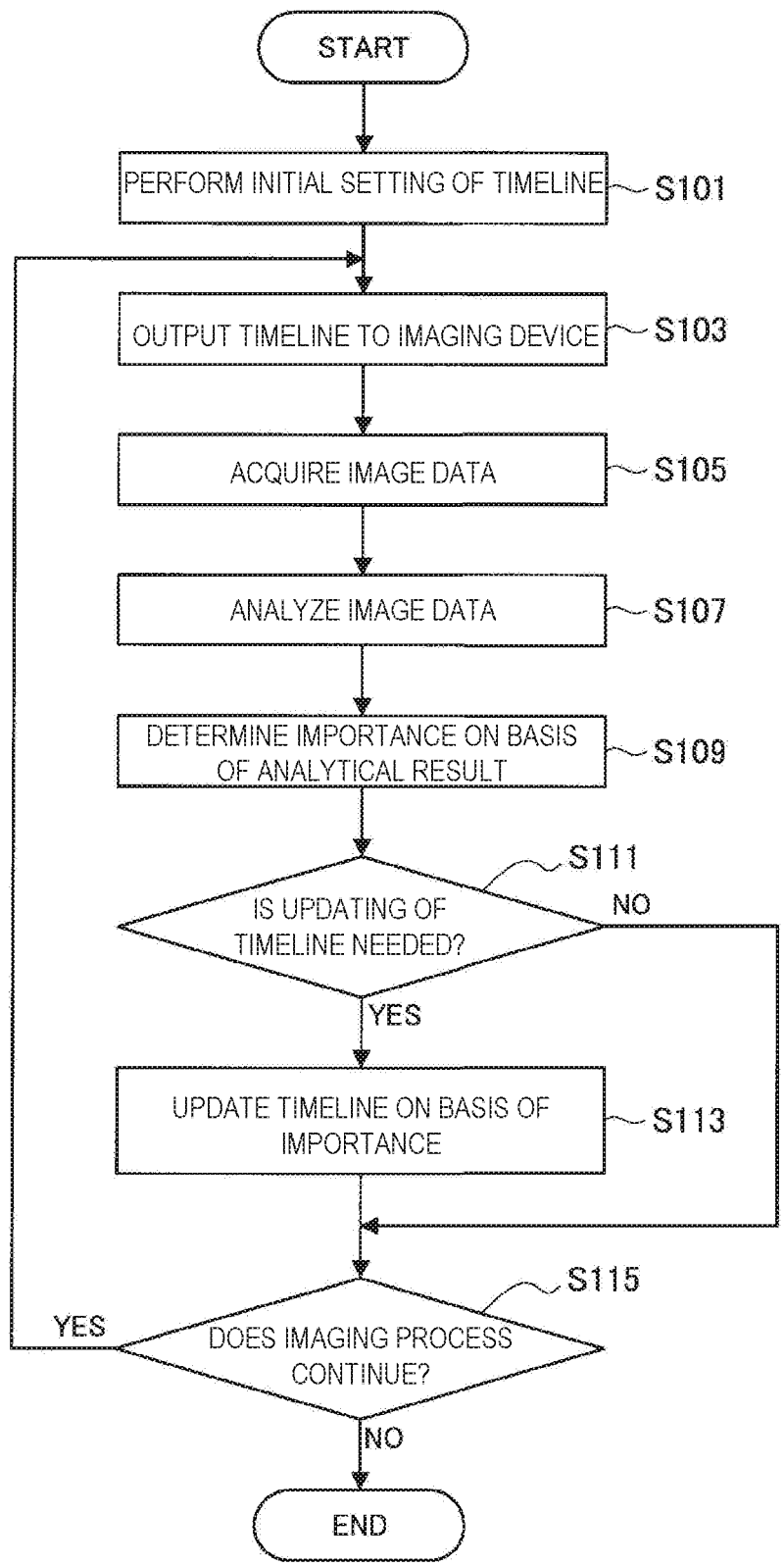
FIG. 12 is a flowchart illustrating an exemplary process performed by an information processing device according to the embodiment.

FIG. 12 is a flowchart illustrating an exemplary process performed by the information processing device 20 according to the first embodiment of the present disclosure. The flowchart in FIG. 12 illustrates an exemplary flow of processes initiated at the start point of the imaging process carried out by the imaging device 10, followed by acquisition of image data from the imaging device 10 by the information processing device 20, determination of the importance on the basis of analytical result (feature) of image data, and setting for the target of generation using the determination result of importance.

First, prior to the imaging process, the setting unit 204 performs initial setting of timeline in the imaging process (step S101). The timeline to be initially set is a timeline typically shown in FIG. 6 as timeline TL1, whose target temporal unit has not yet been updated on the basis of the importance. Next, the output control unit 205 outputs the timeline to the imaging control unit 102 of the imaging device 10 (step S103). The imaging control unit 102 controls the imaging process on the basis of the acquired timeline.

Next, the image acquisition unit 201 acquires, from the imaging device 10, the image data regarding cells produced by the imaging process (step S105). Next, the image analysis unit 202 analyzes the acquired image data, and calculate a feature as an analytical result (step S107).

Next, the determination unit 203 discriminates a cell-specific event expressed in the image data using the calculated feature, and determines the importance (step S109). The setting unit 204 determines whether the timeline is updated or not, on the basis of the determination result of importance (step S111). If the timeline need be updated (S111/YES), the setting unit 204 updates the timeline (step S113).

If the imaging process is sustained (step S115/YES), output control unit 205 outputs the updated timeline to the imaging device 10 (S103). While the imaging process is carried out by the imaging device 10, the information processing device 20 appropriately repeats the processes shown in step S103 to step S115. This enables updating of the timeline in a real-time manner.

The first embodiment of the present disclosure has been explained.

3. SECOND EMBODIMENT

Figure 13:
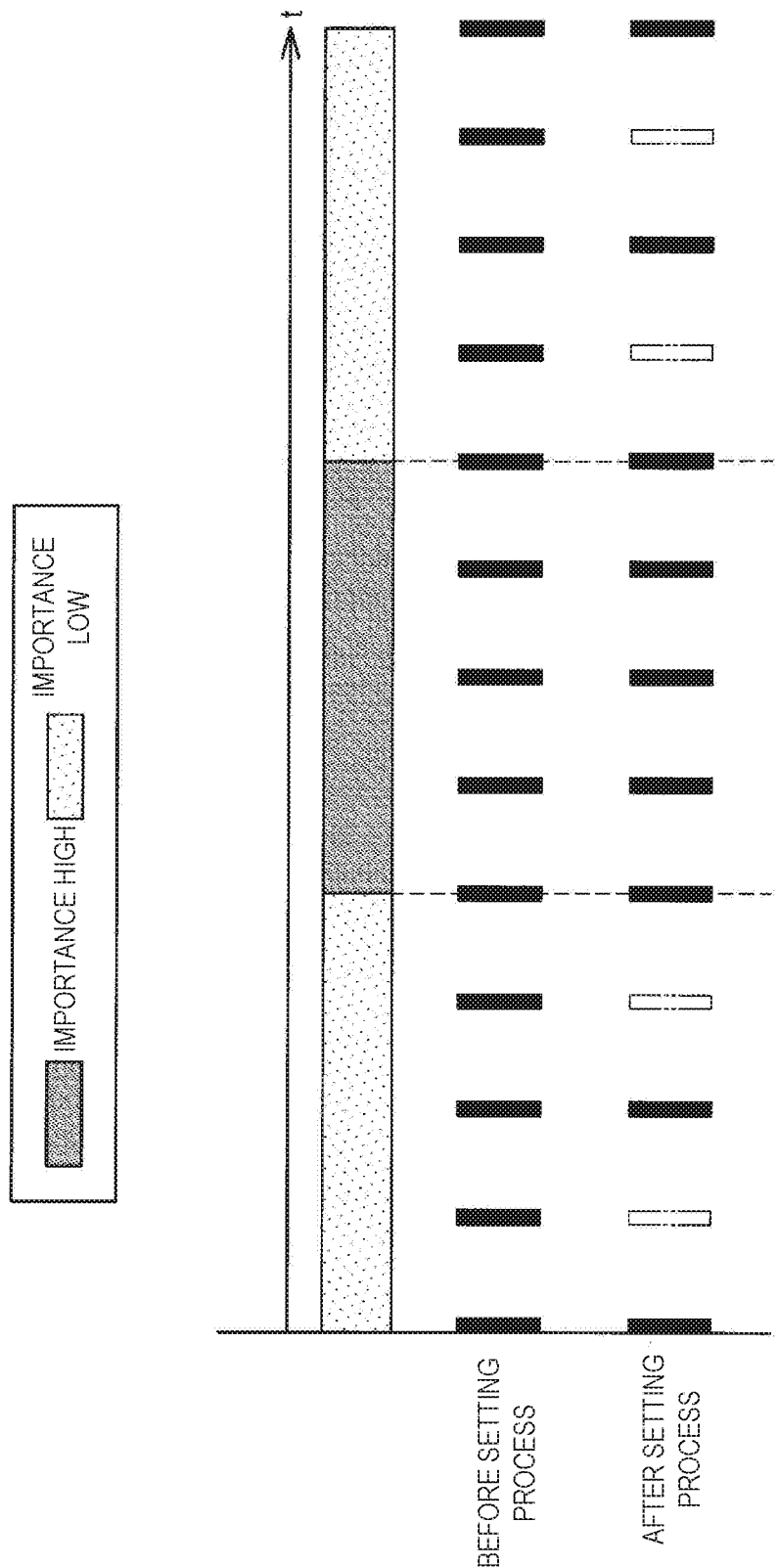
FIG. 13 is a graph illustrating an exemplary setting for a target of generation, carried out by the setting unit according to the second embodiment of the present disclosure.

Next, a second embodiment of the present disclosure will be explained referring to FIG. 13 and FIG. 14. In the information processing system 1 according to this embodiment, carried out is a process regarding setting of a target of storage of image data produced in the imaging process carried out by the imaging device 10. That is, in the information processing system 1 according to the first embodiment of the present disclosure, the image data which will be generable in the future has been processed concurrently with the imaging process carried out by the imaging device 10. In contrast in the information processing system 1 according to this embodiment, the image data that is produced and once accumulated in the storage unit 220 or the like can directly be processed. This enables selective storage of the image data which is considered to be important, among from the image data captured in the imaging process. The image data may therefore be stored efficiently and more exactly, without overloading the user.

Note that the process held by the information processing device 20 according to this embodiment may take place after the imaging device 10 completed the imaging process, or may take place concurrently with the imaging process by the imaging device 10, targeting the image data having been produced in advance and stored in the storage unit 220 or the like.

<3.1. Exemplary Configuration>

Configuration of the information processing device 20 according to this embodiment is identical to the configuration of the information processing device 20 according to the first embodiment of the present disclosure illustrated in FIG. 2. The paragraphs below will explain functions that are different from those of the information processing device 20 according to the first embodiment of the present disclosure.

(Image Acquisition Unit)

The image acquisition unit 201 according to this embodiment has a function of acquiring image data produced in the time-series imaging process targeting a cell. Such image data is stored in the storage unit 220. The image acquisition unit 201 may sequentially acquire the image data from the imaging device 10 when the imaging process by the imaging device 10 is underway, or may acquire the image data from the imaging device 10 after completion of the imaging process by the imaging device 10. The thus acquired image data is subjected to image analysis by the image analysis unit 202, from which a feature regarding the image data can be calculated.

(Determination Unit)

The determination unit 203 can determine the importance on the basis of the thus calculated feature. Technique for the determination process by the determination unit 203 is identical to that in the first embodiment of the present disclosure.

The determination process by the determination unit 203 according to this embodiment is carried out for each of the plurality of image data produced by the time-series imaging process. Hence the setting unit 204 in the succeeding stage can rank the timeline of the time-series imaging process (the timeline herein means time-series information of produced image data after completion of the time-series imaging process, such as time point of generation, or the number of shots of image data) according to the importance, and can preset the target temporal unit.

Note that the image data determined by the determination unit 203 may be all image data produced in the time-series imaging process, or may be image data partially extracted from the timeline of the imaging process.

Alternatively, the determination unit 203 may correlate the image data having been subjected to the determination process, with the determination result of importance. Hence in the setting process of target temporal unit in the setting unit 204 in the succeeding stage, it now becomes possible to preset the target temporal unit on the basis of the time point of generation of image data.

(Setting Unit)

The setting unit 204 has a function of performing setting for the target of acquisition of image data in the time-series imaging process, on the basis of determination result of importance. The setting for the target of acquisition of image data performed by the setting unit 204 according to this embodiment means two types of process, namely (1) setting for target temporal unit, and (2) setting for target of storage (target of acquisition).

(1) Setting for Target Temporal Unit

The setting unit 204 according to this embodiment sets the target temporal unit regarding setting for the target of storage of the produced image data, on the basis of the process period of imaging process carried out by the imaging device 10. Meaning of the setting for the target temporal unit is same as that in the first embodiment of the present disclosure.

The setting unit 204 may sequentially preset the target temporal unit, on the basis of the importance determined using the sequentially acquired image data, in the same way as in the first embodiment of the present disclosure. Such setting process can be carried out in a case where the imaging process and the storage process of image data take place concurrently. Alternatively, the setting unit 204 according to this embodiment may preset the target temporal unit, on the basis of the time point of generation of image data and the importance correlated to the image data, as described above. In this way, the target temporal unit ranked by the importance can be preset more finely.

(2) Setting for Target of Storage

Also, the setting unit 204 according to this embodiment presets the target of storage of image data in the time-series imaging process. Now the setting for target of storage of image data means the setting for a target image data (target of storage) to be stored, among from the image data produced in the time-series imaging process, or setting for decreasing the data size of the produced image data.

The setting for target of storage in this embodiment means, for example, reduction of the target of storage, among from the image data produced in the imaging process according to the timeline. FIG. 13 is a graph illustrating an exemplary setting for the target of generation carried out by the setting unit 204 according to this embodiment. Referring to FIG. 13, the image data is produced at regular intervals of timing of imaging in the time-series imaging process. Upon completion of the imaging process, the importance is determined by the determination unit 203, and the target temporal unit is preset by the setting unit 204. Then in the example illustrated in FIG. 13, the setting unit 204 presets a part of image data in a temporal unit with "low" importance, as a target of reduction. Then the image data preset as the target of reduction can be deleted from the storage unit 220, by the output control unit 205 in the succeeding stage. In this way, the image data regarding the cell-specific events which are not important in observation of cells, may be suppressed from being accumulated.

In addition, similarly to the first embodiment of the present disclosure, in a case where image data of Z-stack image is generable in the time-series imaging process, the setting for the target of storage may include the number of shots (number of acquisition) and focal position of the Z-stack image. For example, the setting unit 204 can make the setting so as to reduce the number of storage (for example, 1 shot) of image data in the target temporal unit with "low" importance. In this process, the setting can be made also regarding that the image data captured at which focal position will be stored. Specific setting for focal position can be made typically depending on types or cell-specific events of cell assumed as the target to be observed. In this way, the image data regarding the cell-specific events which are not important in observation of cells, may be suppressed from being accumulated.

In addition, also a process regarding reduction of data size of the stored image data can be carried out, in the same way as in the first embodiment of the present disclosure. The reduction of data size of the stored image data means, for example, reduction of resolution of the stored image data, or increase of the compressibility. More specifically, the setting unit 204 may set low resolution or high compressibility for image data stored in the temporal unit with low importance. In this way, the data size of image data regarding the cell-specific events which are not important in observation of cells, may be reduced.

As described above, as a result of the setting for the target temporal unit corresponded to the importance carried out by the setting unit 204, the image data primarily containing the time-lapse image that represents the target cell-specific event to be observed may be acquired in an exact and efficient manner.

(Output Control Unit)

The output control unit 205 according to this embodiment controls an output process on the basis of preset items regarding the target of storage set by the setting unit 204. For example, the output control unit 205 may make control so as to delete image data assumed as the target of deletion, among from the image data accumulated in the storage unit 220. Alternatively, the output control unit 205 may make control for reducing the data size of image data assumed as the target of storage.

Note that the output control unit 205 may output information regarding setting for the target of storage to the imaging device 10. In this way, the imaging control unit 102 can delete image data assumed as the target of deletion, among from the image data accumulated in the unillustrated storage unit of the imaging device 10.

The configuration of the control unit 200 according to this embodiment has been explained. With the aid of the individual functional units equipped to such control unit 200, the setting process for the target of storage of image data, accumulated in the imaging process carried out by the imaging device 10, takes place on the basis of the importance obtained as a result of the determination process using the image data. In this way, it becomes possible to efficiently and exactly store only image data that represents the cell-specific events that are desired to be observed, among from a huge volume of image data having been accumulated over a long period, without overloading the user.

<3.2. Exemplary Processing>

The configuration and the functions of the information processing device 20 according to the embodiment have been described above. Next, an exemplary process performed by the information processing device 20 according to the embodiment will be described referring to FIG. 14.

Figure 14:
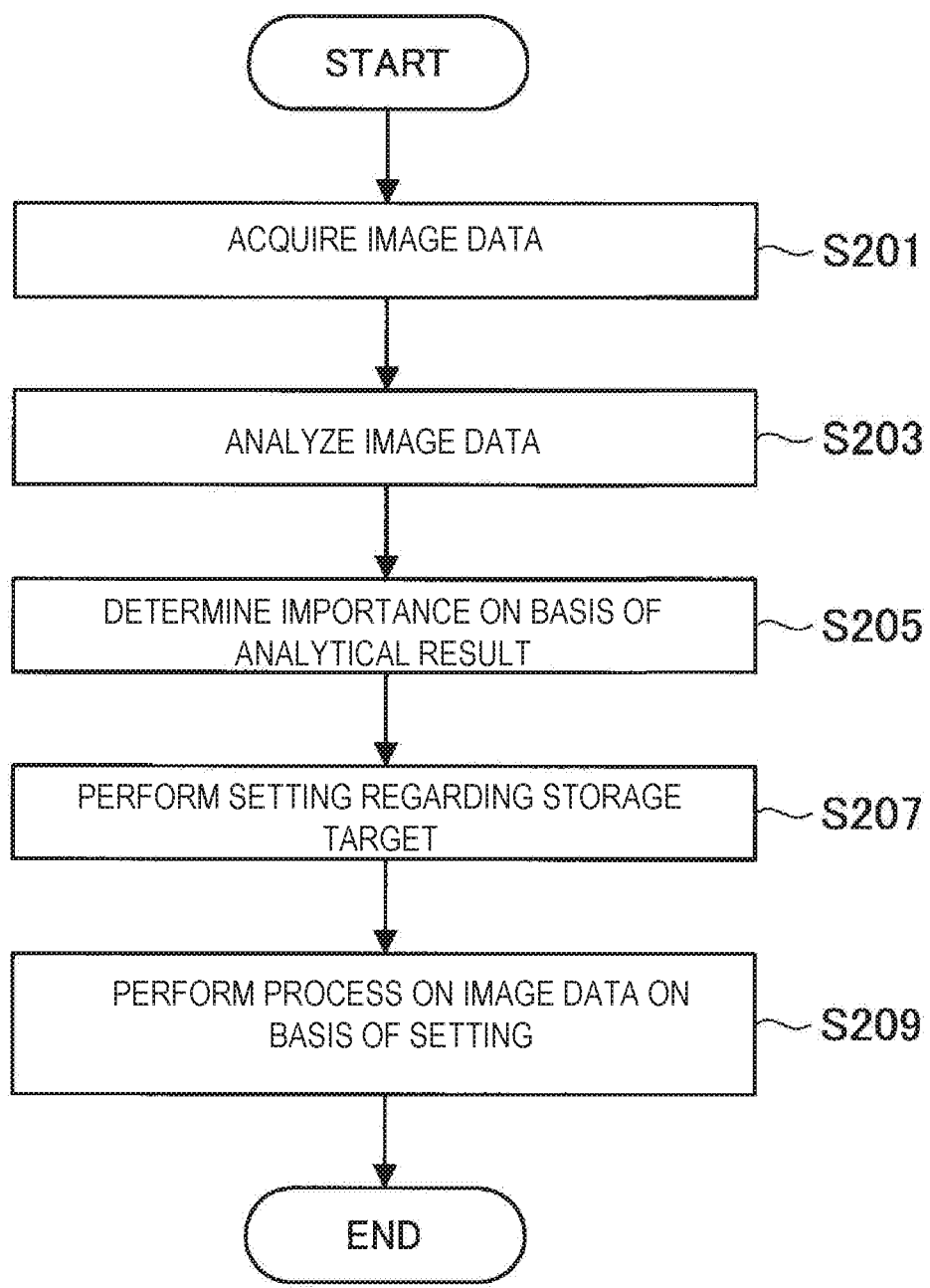
FIG. 14 is a flowchart illustrating an exemplary process performed by an information processing device according to the embodiment.

FIG. 14 is a flowchart illustrating an exemplary process performed by an information processing device 20 according to the second embodiment of the present disclosure. The flowchart illustrated in FIG. 14 illustrates an exemplary flow of processes in which, upon completion of the imaging process by the imaging device 10, the information processing device 20 acquires a series of image data in the time-series imaging process from the imaging device 10, determines the importance according to the analytical result (feature) of the individual image data, and presets the target of storage using the determination result of importance.

First, upon completion of the imaging process, the image acquisition unit 201 acquires the image data regarding cells, having been produced by the imaging process and then accumulated, from the storage unit 220 (or from the imaging device 10) (step S201). Next, the image analysis unit 202 analyzes the acquired image data, and calculate a feature as an analytical result (step S203).

Next, the determination unit 203 discriminates a cell-specific event expressed in each of the image data using the calculated feature, and determines the importance (step S205). Next, the setting unit 204 carries out a process regarding setting for the target of storage, on the basis of the determination result of importance (step S207). The output control unit 205 then carries out a process for image data, such as deletion of image data assumed as the target of deletion, or reduction of data size of image data assumed as the target of storage, depending on the items of setting regarding the target of storage (step S209).

An exemplary process carried out by the information processing device 20 according to this embodiment has been explained. Note that the flowchart illustrated in FIG. 14 is on the premise of a post-process that takes place after all image data were acquired. For example, by appropriately repeating the processes assigned to step S201 to S209, these processes may be carried out concurrently with the imaging process, in a real-time manner.

The second embodiment of the present disclosure has been explained above.

4. EXEMPLARY HARDWARE CONFIGURATION

Next, with reference to FIG. 15, a hardware configuration of an information processing device according to an embodiment of the present disclosure is described. FIG. 15 is a block diagram illustrating an exemplary hardware configuration of the information processing device according to the embodiment of the present disclosure. An illustrated information processing device 900 can realize the information processing device 20 in the above described embodiment.

The information processing device 900 includes a CPU 901, read only memory (ROM) 903, and random access memory (RAM) 905. In addition, the information processing device 900 may include a host bus 907, a bridge 909, an external bus 911, an interface 913, an input device 915, an output device 917, a storage device 919, a drive 921, a connection port 925, and a communication device 929. The information processing device 900 may include a processing circuit such as a digital signal processor (DSP) or an application-specific integrated circuit (ASIC), instead of or in addition to the CPU 901.

The CPU 901 functions as an arithmetic processing device and a control device, and controls the overall operation or a part of the operation of the information processing device 900 according to various programs recorded in the ROM 903, the RAM 905, the storage device 919, or a removable recording medium 923. For example, the CPU 901 controls overall operations of respective function units included in the information processing device 20 of the above-described embodiment. The ROM 903 stores programs, operation parameters, and the like used by the CPU 901. The RAM 905 transiently stores programs used when the CPU 901 is executed, and parameters that change as appropriate when executing such programs. The CPU 901, the ROM 903, and the RAM 905 are connected with each other via the host bus 907 configured from an internal bus such as a CPU bus or the like. The host bus 907 is connected to the external bus 911 such as a Peripheral Component Interconnect/Interface (PCI) bus via the bridge 909.

The input device 915 is a device operated by a user such as a mouse, a keyboard, a touchscreen, a button, a switch, and a lever. The input device 915 may be a remote control device that uses, for example, infrared radiation and another type of radio waves. Alternatively, the input device 915 may be an external connection device 927 such as a mobile phone that corresponds to an operation of the information processing device 900. The input device 915 includes an input control circuit that generates input signals on the basis of information which is input by a user to output the generated input signals to the CPU 901. The user inputs various types of data and indicates a processing operation to the information processing device 900 by operating the input device 915.

The output device 917 includes a device that can visually or audibly report acquired information to a user. The output device 917 may be, for example, a display device such as an LCD, a PDP, and an OELD, an audio output device such as a speaker and a headphone, and a printer. The output device 917 outputs a result obtained through a process performed by the information processing device 900, in the form of text or video such as an image, or sounds such as audio sounds.

The storage device 919 is a device for data storage that is an exemplary storage unit of the information processing device 900. The storage device 919 includes, for example, a magnetic storage device such as a hard disk drive (HDD), a semiconductor storage device, an optical storage device, or a magneto-optical storage device. The storage device 919 stores therein the programs and various data executed by the CPU 901, and various data acquired from an outside.

The drive 921 is a reader/writer for the removable recording medium 923 such as a magnetic disk, an optical disc, a magneto-optical disk, and a semiconductor memory, and built in or externally attached to the information processing device 900. The drive 921 reads out information recorded on the mounted removable recording medium 923, and outputs the information to the RAM 905. The drive 921 writes the record into the mounted removable recording medium 923.

The connection port 925 is a port used to directly connect devices to the information processing device 900. The connection port 925 may be a Universal Serial Bus (USB) port, an IEEE1394 port, or a Small Computer System Interface (SCSI) port, for example. The connection port 925 may also be an RS-232C port, an optical audio terminal, a High-Definition Multimedia Interface (HDMI (registered trademark)) port, and so on. The connection of the external connection device 927 to the connection port 925 makes it possible to exchange various kinds of data between the information processing device 900 and the external connection device 927.

The communication device 929 is a communication interface including, for example, a communication device for connection to a communication network NW. The communication device 929 may be, for example, a wired or wireless local area network (LAN), Bluetooth (registered trademark), or a communication card for a wireless USB (WUSB). The communication device 929 may also be, for example, a router for optical communication, a router for asymmetric digital subscriber line (ADSL), or a modem for various types of communication. For example, the communication device 929 transmits and receives signals in the Internet or transits signals to and receives signals from another communication device by using a predetermined protocol such as TCP/IP. The communication network NW to which the communication device 929 connects is a network established through wired or wireless connection. The communication network NW is, for example, the Internet, a home LAN, infrared communication, radio wave communication, or satellite communication.

Note that the CPU 901, the ROM 903 and the RAM 905 and so forth can enable the functions of the control unit 200 according to the embodiment. Meanwhile the storage device 919 can enable the function of the storage unit 220 according to the embodiment. Moreover, at least either the connection port 925 or the communication device 929 can enable the function of the communication unit 210 according to the embodiment.

The example of the hardware configuration of the information processing device 900 has been introduced.

5. CONCLUSION

The preferred embodiment (s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, although the information processing system 1 is configured to be provided with the imaging device 10 and information processing device 20 in the above-described embodiment, the present technology is not limited thereto. For example, the imaging device 10 may have the function of the information processing device 20 (For example, functions regarding image analysis process, determination process, and setting process or the like). In this case, the information processing system 1 is embodied by the imaging device 10. In addition, the information processing device 20 may have the function of the imaging device 10 (imaging function). In this case, the information processing system 1 is embodied by the information processing device 20. Further, the imaging device 10 may have a part of the function of the information processing device 20, and the information processing device 20 may have a part of the function of the imaging device 10.

Note that the information processing system 1 according to the individual embodiments assumed embryo, which is an exemplary cell, as a target of application. The embryo as a target of application is not limited to human embryo, but may also be embryo of mammals such as mouse, embryo of non-mammalian animal, or embryo of non-animal multicellular organism. Also note, as described above, the information processing system 1 according to one embodiment of the present disclosure is applicable not only to embryo, but also to a wide variety of cells including cancer cell and iPS cell.

The steps in the processes performed by the information processing device in the present specification may not necessarily be processed chronologically in the orders described in the flowcharts. For example, the steps in the processes performed by the information processing device may be processed in different orders from the orders described in the flowcharts or may be processed in parallel.

Also, a computer program causing hardware such as the CPU, the ROM, and the RAM included in the information processing device to carry out the equivalent functions as the above-described configuration of the information processing device can be generated. Also, a readable recording medium having the computer program stored therein can be provided.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing device including:

a determination unit that determines importance related to a cell-specific event of a cell, using image data obtained from a time-series imaging process targeting the cell; and a control unit that controls a process regarding setting for a target of acquisition of image data in the time-series imaging process, on the basis of a determination result of the importance.

(2)

The information processing device according to (1), in which the process regarding the setting for a target of acquisition of image data includes a process that presets the target of acquisition of image data in the time-series imaging process, on the basis of the determination result of importance.

(3)

The information processing device according to (2), in which the process that presets the target of acquisition of image data includes a process that presets time point of generation, in the time-series imaging process, of the image data assumed as the target of acquisition.

(4)

The information processing device according to (2) or (3), in which, in a case where a plurality of image data with different focal positions is generable at one time point in the time-series imaging process, the process that presets the target of acquisition of image data includes a process that presets the number of acquisition of image data at the one time point and/or the focal positions.

(5)

The information processing device according to any one of (1) to (4), in which the process regarding the setting for a target of acquisition of image data includes a process that deletes the target of acquisition in the time-series imaging process.

(6)

The information processing device according to any one of (1) to (5), in which the process regarding the setting for a target of acquisition of image data includes a process that excludes image data acquired at a predetermined time point and thereafter in the time-series imaging process, from the target of acquisition.

(7)

The information processing device according to any one of (1) to (6), in which the process regarding the setting for a target of acquisition of image data controls a process regarding increase or decrease of data size of the image data preset as a target of acquisition, on the basis of the determination result of importance.

(8)

The information processing device according to any one of (1) to (7), in which the process regarding the setting for a target of acquisition of image data includes a process that updates time-series information that specifies the target of acquisition of image data in the time-series imaging process.

(9)

The information processing device according to (8), in which the process that updates time-series information includes a process that deletes the target of acquisition of image data from the time-series information, and/or a process that adds the target of acquisition of image data to the time-series information.

(10)

The information processing device according to any one of (1) to (9), in which the process regarding the setting for a target of acquisition of image data includes a process regarding the setting for a target of storage of image data generated by the time-series imaging process.

(11)

The information processing device according to any one of (1) to (10), in which the control unit presets a target temporal unit targeted by the process regarding the setting for a target of acquisition of image data, out from a process period of the time-series imaging process, corresponding to the importance.

(12)

The information processing device according to (11), in which length of the target temporal unit includes length determined corresponding to the cell-specific event related to the determined importance.

(13)

The information processing device according to (11) or (12), in which length of the target temporal unit includes length determined on the basis of feature obtained by analyzing the image data.

(14)

The information processing device according to any one of (1) to (13), in which the determination unit determines the importance using a feature obtained by analyzing the image data.

(15)

The information processing device according to (14), in which the determination unit discriminates a cell-specific event regarding the cell contained in the image data, on the basis of the feature, and determines the importance on the basis of the discrimination result.

(16)

The information processing device according to (15), in which the importance is estimated using a learned model that has learned a preliminarily acquired relation between the cell-specific event retarding the cell contained in the image data, and feature obtained by analyzing the image data.

(17)

The information processing device according to any one of (13) to (16), in which the feature includes a feature estimated on the basis of at least any one of morphology of image and kinetics of the cell contained in the image data, and pixel of the image data.

(18)

An information processing method including by a processor:

determining importance related to a cell-specific event of a cell, using image data obtained from a time-series imaging process targeting the cell; and controlling a process regarding setting for a target of acquisition of image data in the time-series imaging process, on the basis of a determination result of the importance.

(19)

An information processing system including:
an imaging device that includes
an imaging unit that produces an image by image capturing;
and
an information processing device that includes
a determination unit that determines importance related to a cell-specific event of a cell, using image data obtained from a time-series imaging process targeting the cell by the imaging unit; and
a control unit that controls a process regarding setting for a target of acquisition of image data in the time-series imaging process, on the basis of a determination result of the importance.

REFERENCE SIGNS LIST

1 information processing system
10 imaging device
20 information processing device
101 imaging unit
102 imaging control unit
200 control unit
201 image acquisition unit
202 image analysis unit
203 determination unit
204 setting unit
205 output control unit
210 communication unit
220 storage unit

The invention claimed is:

1. An information processing device comprising:
circuitry configured to:
determine importance of a cell-specific event of a cell, based on image data obtained from a time-series imaging process that targets the cell, wherein a determination result of the determined importance is one of a first importance and a second importance;
control a setting process for a target of acquisition of image data in the time-series imaging process, based on the determination result of the determined importance;
rank a timeline of a process period of the time-series imaging process based on the determination result of the determined importance; and
preset a time zone, of the ranked timeline, that has the first importance as a target temporal unit, wherein the setting process for the target of acquisition of image data targets the target temporal unit.

2. The information processing device according to claim 1, wherein the first importance is one of a high importance and a low importance.

3. The information processing device according to claim 1, wherein the setting process for the target of acquisition of image data includes a setting process to preset time point of generation, in the time-series imaging process, of the image data assumed as the target of acquisition.

4. The information processing device according to claim 1, wherein
the setting process for the target of acquisition of image data includes a setting process to preset a number of acquisitions of image data with different focal positions at one time point in the time-series imaging process, and
wherein a plurality of image data with the different focal positions is generated at the one time point in the time-series imaging process based on the preset number of acquisitions of image data.

5. The information processing device according to claim 1, wherein the setting process for the target of acquisition of image data includes a setting process to delete the target of acquisition in the time-series imaging process.

6. The information processing device according to claim 1, wherein the setting process for the target of acquisition of image data includes a setting process to exclude image data acquired at a predetermined time point and thereafter in the time-series imaging process, from the target of acquisition.

7. The information processing device according to claim 1, wherein the setting process for the target of acquisition of image data includes a setting process to increase or decrease data size of the image data that is preset as the target of acquisition in the target temporal unit based on the determination result of the determined importance.

8. The information processing device according to claim 1, wherein the setting process for the target of acquisition of image data includes a setting process to update time-series information that specifies the target of acquisition of image data in the time-series imaging process.

9. The information processing device according to claim 8, wherein the setting process to update the time-series information includes a first setting process to delete the target of acquisition of image data from the time-series information, and/or a second setting process to add the target of acquisition of image data to the time-series information.

10. The information processing device according to claim 1, wherein the setting process for the target of acquisition of image data includes a setting process for a target of storage of image data generated by the time-series imaging process.

11. The information processing device according to claim 1, wherein the circuitry is further configured to:
update the target temporal unit based on the determination result of the determined importance, wherein the update of the target temporal unit corresponds to a control of a length of the target temporal unit; and
update the timeline based on the update of the target temporal unit.

12. The information processing device according to claim 1, wherein a length of the target temporal unit includes a length of the cell-specific event related to the determination result of the determined importance.

13. The information processing device according to claim 1, wherein a length of the target temporal unit includes a length determined based on a feature obtained by analysis of the image data.

14. The information processing device according to claim 1, wherein the circuitry is further configured to determine the importance based on a feature obtained by analysis of the image data.

15. The information processing device according to claim 14, wherein the circuitry is further configured to discriminate the cell-specific event of the cell contained in the image data, based on the feature, and wherein the determination of the importance is based on a discrimination result.

16. The information processing device according to claim 15, wherein the importance is determined based on a learned model that has learned a preliminarily acquired relation between the cell-specific event of the cell contained in the image data, and the feature obtained by analysis of the image data.

17. The information processing device according to claim 13, wherein the feature includes a feature obtained based on at least any one of morphology of image and kinetics of the cell contained in the image data, and pixel of the image data.

18. An information processing method comprising:
determining, by circuitry, importance of a cell-specific event of a cell, based on image data obtained from a time-series imaging process that targets the cell, wherein a determination result of the determined importance is one of a first importance and a second importance;
controlling, by the circuitry, a setting process for a target of acquisition of image data in the time-series imaging process, based on the determination result of the determined importance;
ranking, by the circuitry, a timeline of a process period of the time-series imaging process based on the determination result of the determined importance; and
presetting, by the circuitry, a time zone of the ranked timeline that has the first importance as a target temporal unit, wherein the setting process for the target of acquisition of image data targets the target temporal unit.

19. An information processing system comprising:
an imaging device that includes
first circuitry configured to produce an image by image capturing; and
an information processing device that includes
second circuitry configured to:
determine importance of a cell-specific event of a cell, based on image data obtained from a time-series imaging process that targets the cell, wherein a determination result of the determined importance is one of a first importance and a second importance;
control a setting process for a target of acquisition of image data in the time-series imaging process, based on the determination result of the determined importance;
rank a timeline of a process period of the time-series imaging process based on the determination result of the determined importance; and
preset a time zone, of the ranked timeline, that has the first importance as a target temporal unit, wherein the setting process for the target of acquisition of image data targets the target temporal unit.

* * * * *